US009868798B2

(12) United States Patent
Musa et al.

(10) Patent No.: US 9,868,798 B2
(45) Date of Patent: Jan. 16, 2018

(54) AMIC ACIDS AND IMIDES DERIVED FROM TERPOLYMERS

(71) Applicant: ISP Investments LLC, Wilmington, DE (US)

(72) Inventors: Osama M. Musa, Bedminster, NJ (US); Krishnamurthy Nacharaju, Hilliard, OH (US); Cristian Grigoras, Suffern, NY (US)

(73) Assignee: ISP Investments LLC, Wilmington, DE (US)

( * ) Notice: Subject to any disclaimer, the term of this patent is extended or adjusted under 35 U.S.C. 154(b) by 0 days.

(21) Appl. No.: 15/126,173

(22) PCT Filed: Mar. 17, 2015

(86) PCT No.: PCT/US2015/020939
§ 371 (c)(1),
(2) Date: Sep. 14, 2016

(87) PCT Pub. No.: WO2015/142832
PCT Pub. Date: Sep. 24, 2015

(65) Prior Publication Data
US 2017/0101485 A1    Apr. 13, 2017

Related U.S. Application Data

(60) Provisional application No. 61/954,000, filed on Mar. 17, 2014.

(51) Int. Cl.
| | |
|---|---|
| *C08F 8/32* | (2006.01) |
| *A61K 8/81* | (2006.01) |
| *A61Q 19/10* | (2006.01) |
| *A61Q 19/00* | (2006.01) |
| *A61Q 5/02* | (2006.01) |
| *A61Q 5/00* | (2006.01) |
| *C09D 131/04* | (2006.01) |
| *C08F 22/36* | (2006.01) |
| *C08F 122/40* | (2006.01) |

(52) U.S. Cl.
CPC ............ *C08F 8/32* (2013.01); *A61K 8/8164* (2013.01); *A61Q 5/00* (2013.01); *A61Q 5/02* (2013.01); *A61Q 19/00* (2013.01); *A61Q 19/10* (2013.01); *C08F 22/36* (2013.01); *C08F 122/40* (2013.01); *C09D 131/04* (2013.01)

(58) Field of Classification Search
CPC ........ C08F 222/06; C08F 261/06; C08F 8/32; C08F 8/23; C08F 122/40; C08F 22/36
See application file for complete search history.

(56) References Cited

U.S. PATENT DOCUMENTS

| 2,313,565 | A | * | 3/1943 | McDowell | ............... C08F 8/00 525/327.6 |
|---|---|---|---|---|---|
| 5,214,089 | A | | 5/1993 | Login et al. | |
| 5,567,787 | A | | 10/1996 | Kwak et al. | |
| 5,869,695 | A | | 2/1999 | Ulmer et al. | |
| 5,994,385 | A | * | 11/1999 | Ulmer | ................. A61K 8/8164 424/401 |
| 2005/0032929 | A1 | * | 2/2005 | Greener | ................... C08F 8/00 523/113 |

FOREIGN PATENT DOCUMENTS

| WO | WO2013082359 A1 | 6/2013 |
|---|---|---|
| WO | WO2013134755 A1 | 9/2013 |

OTHER PUBLICATIONS

International Search Report, WO 2015/142832 Published on Sep. 24, 2015.

* cited by examiner

*Primary Examiner* — Gregory Listvoyb
(74) *Attorney, Agent, or Firm* — William J. Davis

(57) ABSTRACT

The present invention provides amic acids and imides derived from a polymer comprising: (a) maleic anhydride, (b) a first $C_1$-$C_7$ alkyl vinyl ether monomer, and (c) a second $C_8$-$C_{30}$ alkyl vinyl ether monomer, wherein the polymer contains an amic acid or an imide group. The polymers containing an amic acid or an imide group of the invention may be employed in a wide variety of compositions, particularly in oral care compositions. Non-limiting generic structures of the amidic polymers are set out below: (I) wherein $R_1$-$R_3$, M, a, b, c, d, e, and f are defined herein.

15 Claims, No Drawings

AMIC ACIDS AND IMIDES DERIVED FROM TERPOLYMERS

BACKGROUND OF THE INVENTION

Field of the Invention

The present invention provides amic acids and imides derived from a polymer comprising: (a) maleic anhydride, (b) a first $C_1$-$C_7$ alkyl vinyl ether monomer, and (c) a second $C_8$-$C_{30}$ alkyl vinyl ether monomer, wherein the polymer contains an amic acid or an imide group. The amic acids and imides of the invention may be employed in a wide variety of compositions, particularly in oral care compositions.

Description of Related Art

Tooth sensitivity or dentin hypersensitivity is caused by the movement of fluid within tiny tubes located in the dentin (the layer of tissue found beneath the hard enamel that contains the inner pulp), which results in nerve irritation. When hard enamel is worn down or gums have receded, tiny tubes on the surface are exposed. These exposed tubes can cause pain and change eating, drinking, and breathing habits. Eating or drinking hot or cold foods and consumption of acid-containing foods and beverages can also cause tooth sensitivity. Bulimia and acid reflux can also result in erosion of hard enamel and sensitivity due to acid in the mouth.

One approach for the treatment of tooth sensitivity is by reducing the sensitivity of tooth nerves through regulation of the triggering process of the nerve. This is generally achieved by altering the chemical environment of the nerve. Background materials on the use of potassium and strontium salts to reduce tooth nerve sensitivity include U.S. Pat. Nos. 3,863,006, 3,888,976, 4,631,185, 4,751,072, 4,990,327, and 3,122,483.

Another approach to treat sensitive teeth is by blocking the dentinal tubules so that dentin flow is reduced; impulses do not reach the nerve thereby reducing or eliminating the pain and discomfort caused by tooth sensitivity. Background materials on the blocking dentinal tubules include U.S. Pat. Nos. 4,634,589, 4,710,372, 4,362,713 and 5,885,551.

Other background materials include U.S. Pat. Nos. 5,188,818, 5,270,031, 4,952,558, and 5,202,112, 6,241,972, and United States Patent Appl No. 2010/00322984.

Traditional methods for reducing dentin hypersensitivity have employed regulating the sensitivity of tooth nerves and blocking the dentinal tubules. However, there is always a need to explore more avenues for better treatment of tooth sensitivity.

SUMMARY OF THE INVENTION

The invention provides amic acids and imides derived from a polymer comprising: (a) maleic anhydride, (b) a first $C_1$-$C_7$ alkyl vinyl ether monomer, and (c) a second $C_8$-$C_{30}$ alkyl vinyl ether monomer, wherein the polymer contains an amic acid or an imide group.

The amic acids and imides may be represented by the following structure:

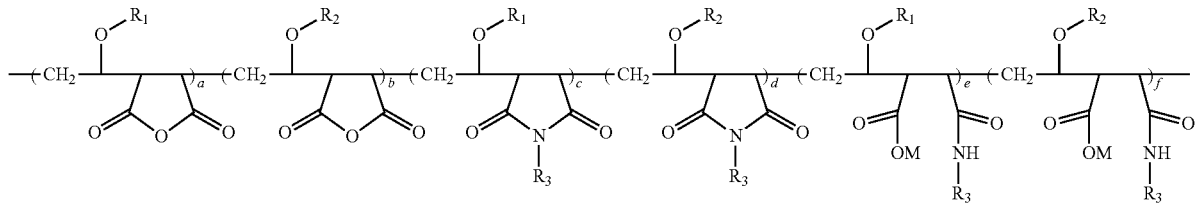

wherein $R_1$ is a $C_1$-$C_7$ alkyl group, $R_2$ is a $C_8$-$C_{30}$ alkyl group, $R_3$ is a $C_1$-$C_{30}$ alkyl group, and M is selected from the group consisting of hydrogen, alkali metals, alkaline earth metals, ammonium salts, and combinations thereof, wherein a, b, c, d, e, and f are molar amounts, the sum of which equals 100%, providing that c and d are not both zero at the same time.

The invention further provides compositions comprising the polymer containing an amic acid or an imide group, wherein the compositions comprise adhesives, aerosols, agricultural compositions, beverages, biocides, cleaning compositions, coating compositions, cosmetic compositions, dental compositions, detergents, drugs, electronics, encapsulations, foods, hair gels, hair sprays, household-industrial-institutional, inks, lithographic solutions, membrane compositions, metal fluids, oilfield compositions, oral care compositions, paints, paper, personal care compositions, pharmaceuticals, plasters, plastics, printing, and wood-care compositions.

DETAILED DESCRIPTION

The invention provides amic acids and imides derived from a polymer comprising: (a) maleic anhydride, (b) a first $C_1$-$C_7$ alkyl vinyl ether monomer, and (c) a second $C_8$-$C_{30}$ alkyl vinyl ether monomer, wherein the polymer contains an amic acid or an imide group.

The amic acids and imides of the invention may be employed in a wide variety of compositions, particularly in oral care compositions. The amic acids and imides may be employed singly or in mixtures, and may be formulated with other ingredients as necessary.

As used herein, the following terms have the meanings set out below.

The term "amic acid" refers to an organic compound containing both a carboxylic acid and an amide functionality.

The term "anion" refers to an ion with more electrons than protons, giving it a net negative charge.

The term "branched and unbranched alkyl groups" refers to alkyl groups, which may be straight chained or branched. For example, the alkyl groups may have from 1 to about 18 carbon atoms, more particularly, from 1 to about 10 carbon atoms, and yet more particularly from 1 to about 6 carbon atoms. Branched groups include isopropyl, tert-butyl, and the like.

The term "cation" refers to an ion with fewer electrons than protons, giving it a net positive charge.

The term "generic substituent(s)" refer(s) to substituent(s) such as $R_1$-$R_3$, and integer subscripts used and defined in the invention.

The term "heteroatom" refers to atoms such as oxygen, nitrogen, sulfur, and phosphorous.

The term "hydrophilic" refers to a molecular entity that tends to be polar and capable of hydrogen bonding, thereby enabling it to be water-soluble or water-miscible.

The term "hydrophobic" refers to a molecular entity that tends to be non-polar and is not water-soluble. Hydrophilic entities dissolve in non-polar solvents.

The term "imide" refers to a functional group consisting of two acyl groups bound to nitrogen. These groups are structurally related to acid anhydrides, although imides are less reactive. Most imides are cyclic compounds derived from dicarboxylic acids and their names reflect the parent acid. Examples are maleimide derived from maleic acid, succinimide derived from succinic acid, and phthalimide derived from phthalic acid.

The term "monomer" refers to the repeat units comprising a polymer. A monomer is a small molecule that can chemically bond to other monomers to form a polymer.

The term "non-homopolymer" refers to a polymer formed from two or more monomers and includes essentially all polymers that are not homopolymers.

The term "polymer" refers to a large molecule (macromolecule) composed of repeating structural units (monomers) connected by covalent chemical bonds.

The term "polymer having a hydroxyl group" refers to a polymer containing the —OH group.

The term "polymeric blend" refers to a mixture of polymers. The particular blend may or may not have a synergistic effect on the particular physical or mechanical properties of the blend and the blend may or may not have inherent internal binding properties, such as hydrogen bonding.

The term "polymerization" refers to methods for chemically reacting monomer compounds to form polymer chains. The polymer chain may be alternating, block, or random. The type of polymerization method may be selected from a wide variety of methods. Such methods include, but are not limited to, free radical polymerization methods, such as classical radical polymerization and controlled radical polymerization, including, but not limited to Nitroxide Mediation Polymerization (NMP), Atom Transfer Radical Polymerization (ATRP), and Reversible Addition Fragmentation Chain-Transfer (RAFT).

The term "radical polymerization" or "free radical polymerization" refers to a method of polymerization by which a polymer is formed from the successive addition of free radical building blocks. Free radicals can be formed via a number of different mechanisms usually involving separate initiator molecules. Following creation of free radical monomer units, polymer chains grow rapidly with successive addition of building blocks onto free radical sites.

The term "respectively" is a term that denotes that the items in a list correspond to each other in the order they are given. With reference to two or more items, the term refers in a parallel or sequential manner.

The term "weight-average molecular weight" refers to a method of describing the molecular weight of a polymer. Polymer molecules, even if of the same type, come in different sizes (chain lengths, for linear polymers), so an average of some kind must be calculated. For the weight-average molecular weight, this is calculated by the equation:

$$\overline{M}w = \frac{\sum_i N_i M_i^2}{\sum_i N_i M_i}$$

where $N_i$ is the number of molecules of molecular weight $M_i$.

The present invention provides polymers comprising: (a) maleic anhydride, (b) a first $C_1$-$C_7$ alkyl vinyl ether monomer, and (c) a second $C_8$-$C_{30}$ alkyl vinyl ether monomer, wherein the polymer contains an amic acid or an imide group.

In one aspect, (b) is a first $C_1$-$C_7$ alkyl vinyl ether monomer. Preferably, the $C_1$-$C_7$ alkyl vinyl ether monomers are $CH_3$ or $C_4H_9$, and mixtures thereof. More preferably, the $C_1$-$C_7$ alkyl vinyl ether monomer is $CH_3$.

In another aspect, (c) is a second $C_8$-$C_{30}$ alkyl vinyl ether monomer. Preferably, the $C_8$-$C_{30}$ alkyl vinyl ether monomers are selected from the group consisting of $C_8H_{17}$, $C_{12}H_{25}$, $C_{16}H_{33}$, and mixtures thereof. More preferably, the $C_8$-$C_{30}$ alkyl vinyl ether monomers are $C_{8H17}$ and $C_{12}H_{25}$, and mixtures thereof.

The combination of the polymers comprising: (a) maleic anhydride, (b) a first $C_1$-$C_7$ alkyl vinyl ether monomer, and (c) a second $C_8$-$C_{30}$ alkyl vinyl ether monomer provide polymers containing an amic acid or an imide group.

In another aspect, the present polymers comprise: (a) a first repeating unit selected from the group consisting of:

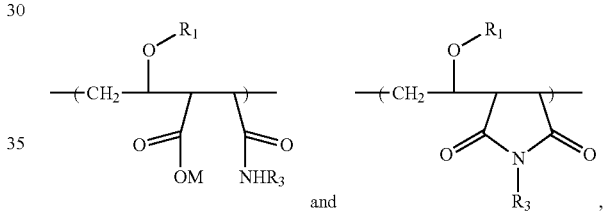

and combinations thereof, and (b) a second repeating unit selected from the group consisting of:

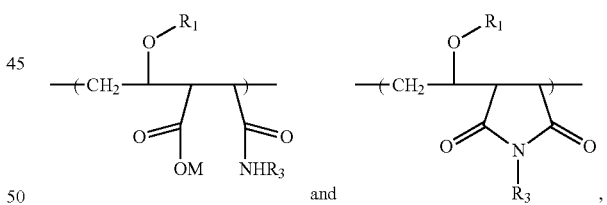

and combinations thereof, wherein $R_1$ is a $C_1$-$C_7$ alkyl group, $R_2$ is a $C_8$-$C_{30}$ alkyl group, $R_3$ is a $C_1$-$C_{30}$ alkyl group, and M is selected from the group consisting of hydrogen, alkali metals, alkaline earth metals, ammonium salts, and combinations thereof.

The polymer, set out above, may further comprise a repeating unit selected from the group consisting of:

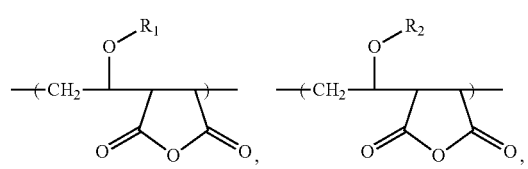

-continued

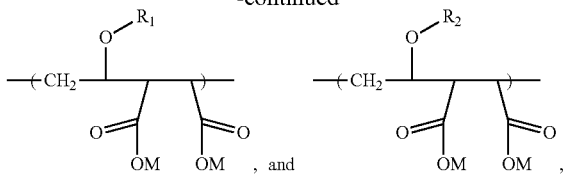, and and combinations thereof; wherein $R_1$ is a $C_1$-$C_7$ alkyl group, $R_2$ is a $C_8$-$C_{30}$ alkyl group, and M is selected from the group consisting of hydrogen, alkali metals, alkaline earth metals, ammonium salts, and combinations thereof. Preferably, $R_1$ is $CH_3$, $R_2$ is $C_{12}H_{25}$, $R_3$ is selected from the group consisting of $C_4H_9$, $C_8H_{17}$, $C_{12}H_{25}$, and $C_{16}H_{33}$, and M is H or Na.

In another aspect, the present polymers may be represented by the following structure:

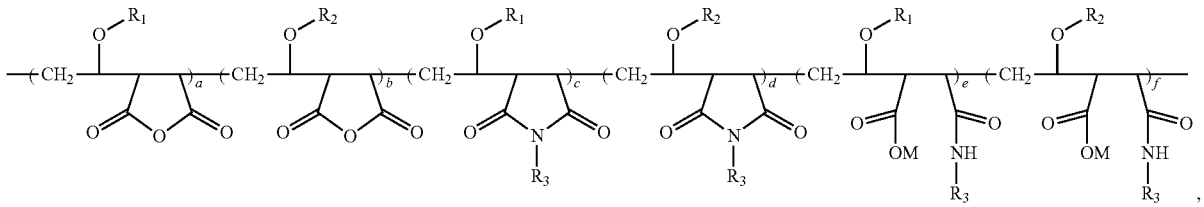

wherein $R_1$ is a $C_1$-$C_7$ alkyl group, $R_2$ is a $C_8$-$C_{30}$ alkyl group, $R_3$ is a $C_1$-$C_{30}$ alkyl group, and M is selected from the group consisting of hydrogen, alkali metals, alkaline earth metals, ammonium salts, and combinations thereof, wherein a, b, c, d, e, and f are molar amounts, the sum of which equals 100%, providing that c and d are not both zero at the same time.

In another aspect, the present polymers may be represented by the following structure:

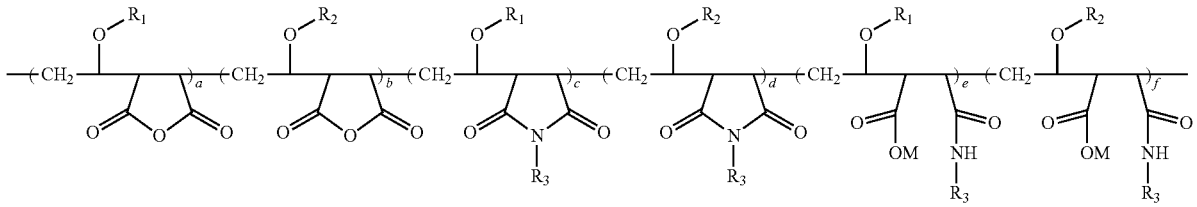

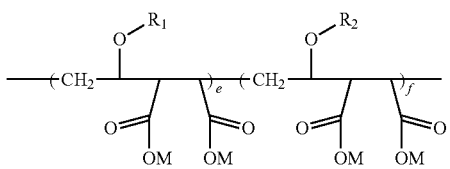

wherein $R_1$ is a $C_1$-$C_7$ alkyl group, $R_2$ is a $C_8$-$C_{30}$ alkyl group, $R_3$ is a $C_1$-$C_{30}$ alkyl group, and M is selected from the group consisting of hydrogen, alkali metals, alkaline earth metals, ammonium salts, and combinations thereof, wherein a, b, c, d, e, and f are molar amounts, the sum of which equals 100%, providing that c and d are not both zero at the same time and e and f are not both zero at the same time.

In a preferred aspect, the present polymers may be represented by the following structures:

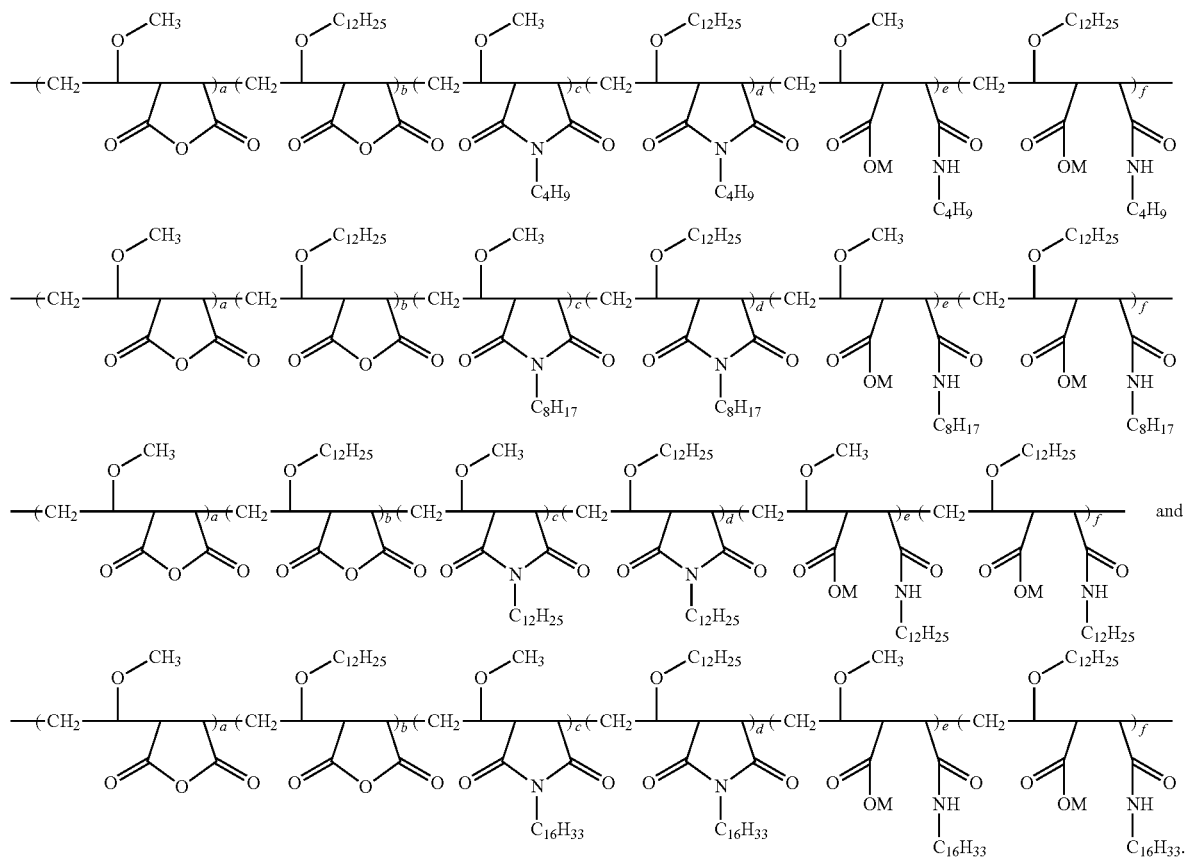

The weight-average molecular weight, as defined above, of the polymer containing an amic acid or an imide group in this embodiment is from about 1,000 to about 10,000,000, preferably from about 10,000 to about 1,000,000, and more preferably from about 10,000 to about 600,000.

As set out above, a, b, c, d, e, and f are molar amounts, the sum of which equals 100%, providing that c and d are not both zero at the same time and e and f are not both zero at the same time. Preferably, a, b, c, d, e, and f independently range from about 1% to about 95%, more preferably from about 5% to about 75%, and most preferable from about 10% to about 50%.

Polymers of the invention may be used in a wide variety of compositions such as in adhesives, agricultural, biocides, coatings, electronics, health care products, household-industrial-institutional (HI&I), inks, membranes, metal fluids, oilfield, paper, paints, plastics, printing, plasters, and wood-care compositions.

Depending on the end application, one or more fillers may be included in the compositions and may be added for improved rheological properties and/or stress reduction. Examples of suitable nonconductive fillers include alumina, aluminum hydroxide, silica, fused silica, fumed silica, vermiculite, mica, wollastonite, calcium carbonate, titania, sand, glass, barium sulfate, zirconium, carbon black, organic fillers, and halogenated ethylene polymers, such as, tetrafluoroethylene, trifluoroethylene, vinylidene fluoride, vinyl fluoride, vinylidene chloride, and vinyl chloride. Examples of suitable conductive fillers include carbon black, graphite, gold, silver, copper, platinum, palladium, nickel, aluminum, silicon carbide, boron nitride, diamond, and alumina. Combinations of these fillers may be used.

The filler particles may be of any appropriate size, particularly from the nano to micro range. The choice of such size for any particular end use is within the expertise of one skilled in the art. The filler may be present in an amount from about 10% to about 90% by weight of the total composition. More than one filler type may be used in a composition and the fillers may or may not be surface treated. Appropriate filler sizes can be determined by the practitioner, and, in particular, may be within the range from about 20 nm to about 100 nm.

Other materials, such as adhesion promoters (e.g. epoxides, silanes), dyes, pigments, and rheology modifiers may be added as desired for the modification of the final properties. Such materials and the amounts needed are within the expertise of those skilled in the art.

Compositions belonging to the personal care/cosmetic and pharmaceutical arts find utility in altering, delivering an active, enhancing, improving, modifying the appearance, condition, color, health, style of the skin (including face, scalp, and lips), hair, nails, and oral cavity. Many examples and product forms of these compositions are known. These compositions can impart benefits that include, but are not limited to, hair style flexibility, hair style durability, humidity resistance for hair, color and/or color protection, moisturization, wrinkle reduction, protection from ultraviolet radiation, water proofness, water resistance, wear resistance, thermal protection, adhesion, active ingredient delivery, anti-cavity, and/or anti-gingivitis protection. As such, these compositions are sometimes categorized in the following areas: skin care, hair care (both styling and non-styling), sun care, cosmetics (including color cosmetics), antiperspirants, deodorants, oral hygiene, and men's and women's personal hygiene/grooming. In some cases these benefits and care areas overlap with another.

Skin care compositions include those materials used on the body, face, hands, lips, and/or scalp, and are beneficial for many reasons, such as firming, anti-cellulite, moisturizing, nourishing, cleaning, reducing or eliminating the appearance of wrinkles or lentigo, toning, and/or purifying. They also can be used to sanitize.

Consumers can identify many of the compositions that serve the sun care area, for example after-fun, children's, beach, self-tan, sports (i.e., being sweat proof, waterproof, resistant to running, or having added UV absorbers and/or antioxidants), sensitive skin products (i.e., having low irritation to the eyes and/or skin, and/or being free of fragrances and/or dyes), daily wear, leave-on hair creams, lotions, styling products, and hair sprays. Typically, sun care products also comprise one or more UV actives, which are those organic and inorganic materials that scatter, absorb, and/or reflect radiation having a wavelength from about 100 nm to about 400 nm. In one aspect, the sun care product protects against UV-A and/or UV-B radiation. UV-A radiation, from about 320 nm to about 400 nm, has the longest wavelength within the UV spectrum, and consequently is the least energetic. While UV-A rays can induce skin tanning, they are liable to induce adverse changes as well, especially in the case of sensitive skin or of skin, which is continually exposed to solar radiation. In particular UV-A rays cause a loss of skin elasticity and the appearance of wrinkles, leading to premature skin aging. UV-B rays have shorter wavelengths, from about 290 nm to about 320 nm, and their higher energy can cause erythema and skin burns, which may be harmful. Alternatively, sun care products may omit UV actives, and may be regarded as a tanning oil or a tan promoter. Some sun care compositions may promote soothe skin after sun exposure, and/or be formulated for application to the lips, hair, or the area around the eyes. Self-tan compositions, which are products that color skin without requiring full sun exposure, also fit under the sun care umbrella. The many different sun care product formats include may assume a consistency ranging from liquid to semiliquid forms (e.g., milks, creams), to thicker forms like gels, creams, pastes, and even solid- and wax-like forms. Sun care products also may take the form of an aerosol, spray, mist, roll-on, or wipe.

Hair care compositions include shampoos, leave-on and rinse-out conditioners used for conditioning, moisturizing, repairing, hair colors, hair relaxers, and deep conditioners and treatments such as hot oils and waxes, 2-in-1 shampoo/conditioner combination products, 3-in-1 shampoo/conditioner/styling agent. The many types of hair care products can be delivered in an array of formats, including aerosol sprays, pump sprays, gel sprays, mousses, gels, waxes, creams, pomades, spritzes, putties, lacquers, de-frizzing serums, perms, relaxants and colorants.

Color cosmetic compositions include facial make-up, eye makeup, mascaras, lip and nail products. Facial make-up compositions include foundation (liquid, solid, and semi-solid)—skin tinted creams, liquid, sticks, mousses used as a base under make-up, rouge, face powder, blusher, highlighters, face bronzers, concealers, and 2-way cake products.

Personal care/cosmetics also include eye make-up, mascaras, eyeliners, eye shadows, eyebrow pencils and eye pencils. Lip products include lipsticks, lip pencils, lip gloss, transparent bases and tinted lip moisturizers as well as multi-function color sticks that can also be used for cheeks and eyes. Nail products include nail varnishes/enamels, nail varnish removers, treatments, home-manicure products such as cuticle softeners and nail strengtheners.

In addition to the skin, hair, and sun care compositions summarized above, the polymers related herein also find application in oral care compositions. Non-limiting examples or oral care compositions include toothpastes (including toothpaste gels), denture adhesives, whiteners, anesthetics, and dental floss and related products. These compositions may take any product format, such as pastes, gels, creams, solutions, dispersions, rinses, flosses, aerosols, powders, and lozenges.

Grooming products for men and women include shaving products and toiletries, which may find use in preparing the skin and/or hair for dry or wet shaving. In addition, these compositions may help to moisturize, cool, and/or soothe skin. A variety of product forms are known, a few of which are foams, gels, creams, sticks, oils, solutions, tonics, balms, aerosols, mists, sprays, and wipes.

The polymer can also be used in other personal care/cosmetic applications, such as an absorbent material in appropriate applications such as diapers, incontinence products, feminine products, and other related products.

The polymers described herein also find application in bath and shower compositions, such as foams, gels, salts, oils, balls, liquids, powders and pearls. Also included are bar soaps, body washes, shower gels, cleansers, gels, oils, foams, scrubs and creams. As a natural extension of this category, these compositions also include liquid soaps and hand sanitizers used for cleaning hands.

The polymer of the invention can be used in combination with one or more additional personal care/cosmetically acceptable additives chosen from, for example, conditioning agents, protecting agents, such as, for example, hydro-soluble, liposoluble and water-insoluble UV filters, antiradical agents, antioxidants, vitamins and pro-vitamins, fixing agents, oxidizing agents, reducing agents, dyes, cleansing agents, anionic, cationic, nonionic and amphoteric surfactants, thickeners, perfumes, pearlizing agents, stabilizers, pH adjusters, filters, hydroxy acids, various cationic, anionic and nonionic polymers, cationic and nonionic polyether associative polyurethanes, preservatives, vegetable oils, mineral oils, synthetic oils, polyols such as glycols and glycerol, silicones, aliphatic alcohols, colorants, bleaching agents, highlighting agents and sequestrants.

These additives may be present in the composition according to the invention in proportions that may range from about 0% to about 20% by weight in relation to the total weight of the composition. An expert in the field according to its nature and its function may easily determine the precise amount of each additive.

Examples of these co-ingredients and many others can be found in the following references, each of which is herein incorporated in its entirety by reference: "Inventory and common nomenclature of ingredients employed in cosmetic products," *Official Journal of the European Union*, May 4, 2006, pages L 97/1 through L 97/528; and *International Cosmetic Ingredient Dictionary and Handbook*, 13$^{th}$ edition, ISBN: 1882621476, published by The Personal Care Products Council in January 2010.

Any known conditioning agent is useful in the personal care/cosmetic compositions of this invention. Conditioning agents function to improve the cosmetic properties of the hair, particularly softness, thickening, untangling, feel, and static electricity and may be in liquid, semi-solid, or solid form such as oils, waxes, or gums. Similarly, any known skin-altering agent is useful in the compositions of this invention. A few examples of conditioning agents include cationic polymers, cationic surfactants and cationic silicones. Conditioning agents may be chosen from synthesis oils, mineral oils, vegetable oils, fluorinated or perfluorinated oils, natural or synthetic waxes, silicones, cationic polymers, proteins and hydrolyzed proteins, ceramide type compounds, cationic surfactants, fatty amines, fatty acids and their derivatives, as well as mixtures of these different compounds.

The cationic polymers that may be used as a conditioning agent according to the invention are those known to improve the cosmetic properties of hair treated by detergent compositions. The expression "cationic polymer" as used herein, indicates any polymer containing cationic groups and/or ionizable groups in cationic groups. The cationic polymers used generally have a number-average molecular weight, which falls between about 500 and 5,000,000, for example between 1000 and 3,000,000. Cationic polymers may be chosen from among those containing units including primary, secondary, tertiary, and/or quaternary amine groups that may either form part of the main polymer chain or a side chain. Useful cationic polymers include known polyamine, polyaminoamide, and quaternary polyammonium types of polymers, such as:

- homopolymers and copolymers derived from acrylic or methacrylic esters or amides. The copolymers can contain one or more units derived from acrylamides, methacrylamides, diacetone acrylamides, acrylic or methacrylic acids or their esters, vinyl lactams such as vinyl pyrrolidone or vinyl caprolactam, and vinyl esters. Specific examples include: copolymers of acrylamide and N,N-dimethylaminoethyl methacrylate quaternized with dimethyl sulfate or with an alkyl halide; copolymers of acrylamide and methacryloyloxyethyl trimethyl ammonium chloride; the copolymer of acrylamide and methacryloyloxyethyl trimethyl ammonium methosulfate; copolymers of vinyl pyrrolidone/dialkylaminoalkyl acrylate or methacrylate, optionally quaternized, such as the products sold under the name Gafquat® by Ashland Specialty Ingredients; the N,N-dimethylaminoethyl methacrylate/vinyl caprolactam/vinyl pyrrolidone terpolymers, such as the product sold under the name Gaffix® VC 713 by Ashland Specialty Ingredients; the vinyl pyrrolidone/methacrylamidopropyl dimethylamine copolymer, marketed under the name Styleze® CC-10 by Ashland Specialty Ingredients; the vinyl pyrrolidone/quaternized dimethyl amino propyl methacrylamide copolymers such as the product sold under the name Gafquat® HS-100 by Ashland Specialty Ingredients; and the vinyl pyrrolidone/dimethylaminopropyl methacrylamide/$C_9$-$C_{24}$ alkyldimethylaminopropyl methacrylic acid quaternized terpolymers described in U.S. Pat. No. 6,207,778 and marketed under the name Styleze® W-20 by Ashland Specialty Ingredients.
- derivatives of cellulose ethers containing quaternary ammonium groups, such as hydroxyethyl cellulose quaternary ammonium that has reacted with an epoxide substituted by a trimethyl ammonium group.
- derivatives of cationic cellulose such as cellulose copolymers or derivatives of cellulose grafted with a hydrosoluble quaternary ammonium monomer, as described in U.S. Pat. No. 4,131,576, such as the hydroxy alkyl cellulose, and the hydroxymethyl-, hydroxyethyl- or hydroxypropyl-cellulose grafted with a salt of methacryloyl ethyl trimethyl ammonium, methacrylamidopropyl trimethyl ammonium, or dimethyl diallyl ammonium.
- cationic polysaccharides such as described in U.S. Pat. Nos. 3,589,578 and 4,031,307, guar gums containing cationic trialkyl ammonium groups and guar gums modified by a salt, e.g., chloride of 2,3-epoxy propyl trimethyl ammonium.
- polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers.
- water-soluble polyamino amides prepared by polycondensation of an acid compound with a polyamine. These polyamino amides may be reticulated.
- derivatives of polyamino amides resulting from the condensation of polyalkylene polyamines with polycarboxylic acids followed by alkylation by bi-functional agents.
- polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers are described in U.S. Pat. Nos. 3,227,615 and 2,961,347.
- the cyclopolymers of alkyl dialyl amine or dialkyl diallyl ammonium such as the homopolymer of dimethyl diallyl ammonium chloride and copolymers of diallyl dimethyl ammonium chloride and acrylamide.
- quaternary diammonium polymers such as hexadimethrine chloride. Polymers of this type are described particularly in U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945, and 4,027,020.
- quaternary polyammonium polymers, including, for example, Mirapol® A 15, Mirapol® AD1, Mirapol® AZ1, and Mirapol® 175 products sold by Miranol.
- the quaternary polymers of vinyl pyrrolidone and vinyl imidazole such as the products sold under the names Luviquat® FC 905, FC 550, and FC 370 by BASF.
- quaternary polyamines.
- reticulated polymers known in the art.

The conditioning agent can be a protein or hydrolyzed cationic or non-cationic protein. Examples of these compounds include hydrolyzed collagens having triethyl ammonium groups, hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having groups of quaternary ammonium on the polypeptide chain, including at least one $C_1$-$C_{18}$ alkyl. Hydrolyzed proteins include Croquat™ L, in which the quaternary ammonium groups include a $C_{12}$ alkyl group, Croquat™ M, in which the quaternary ammonium groups include $C_{10}$-$C_{18}$ alkyl groups, Croquat™ S in which the quaternary ammonium groups include a $C_{18}$ alkyl group and Crotein Q in which the quaternary ammonium groups include at least one $C_1$-$C_{18}$ alkyl group. These products are sold by Croda. The conditioning agent can comprise quaternized vegetable proteins such as wheat, corn, or soy proteins such as cocodimonium hydrolyzed wheat protein, laurdimonium hydrolyzed wheat protein and steardimonium hydrolyzed wheat protein.

The conditioning agent can be a ceramide type of compound such as a ceramide, a glycoceramide, a pseudoceramide, or a neoceramide. These compounds can be natural or synthetic. Compounds of the ceramide type are, for example, described in patents pending DE4424530, DE4424533, DE4402929, DE4420736, WO95/23807, WO94/07844, EP-A-0646572, WO95/16665, FR-2 673 179, EP-A-0227994, WO 94/07844, WO 94/24097, and WO 94/10131. Ceramide type compounds useful herein include 2-N-linoleoyl amino-octadecane-1,3-diol, 2-N-oleoyl amino-octadecane-1,3-diol, 2-N-palmitoyl amino-octadecane-1,3-diol, 2-N-stearoyl amino-octadecane-1,3-diol, 2-N-behenoyl amino-octadecane-1,3-diol, 2-N-[2-hydroxy-palmitoyl]-amino-octadecane-1,3-diol, 2-N-stearoyl amino-octadecane-1,3,4-triol, N-stearoyl phytosphingosine, 2-N-palmitoyl amino-hexadecane-1,3-diol, bis-(N-hydroxy ethyl N-cetyl) malonamide, N(2-hydroxy ethyl)-N-(3-cetoxyl-2-hydroxy propyl) amide of cetylic acid, N-docosanoyl N-methyl-D-glucamine and mixtures of such compounds.

The conditioning agent can be a cationic surfactant such as a salt of a primary, secondary, or tertiary fatty amine, optionally polyoxyalkylenated, a quaternary ammonium salt, a derivative of imadazoline, or an amine oxide. Suitable examples include mono-, di-, or tri-alkyl quaternary ammonium compounds with a counter-ion such as a chloride, methosulfate, tosylate, etc. including, but not limited to, cetrimonium chloride, dicetyldimonium chloride, behentrimonium methosulfate, and the like. The presence of a quaternary ammonium compound in conjunction with the polymer described above reduces static and enhances combing of hair in the dry state. The polymer also enhances the deposition of the quaternary ammonium compound onto the hair substrate thus enhancing the conditioning effect of hair.

The conditioning agent can be any fatty amine known to be useful as a conditioning agent; e.g. dodecyl, cetyl or stearyl amines, such as stearamidopropyl dimethylamine. The conditioning agent can be a fatty acid or derivatives thereof known to be useful as conditioning agents. Suitable fatty acids include myristic acid, palmitic acid, stearic acid, behenic acid, oleic acid, linoleic acid, and isostearic acid. The derivatives of fatty acids include carboxylic esters including mono-, di-, tri- and tetra-carboxylic acids.

The conditioning agent can be a fluorinated or perfluorinated oil. Fluorinated oils include perfluoropolyethers described in EP-A-486135 and the fluorohydrocarbon compounds described in WO 93/11103. The fluoridated oils may also be fluorocarbons such as fluoramines, e.g., perfluorotributylamine, fluoridated hydrocarbons, such as perfluorodecahydronaphthalene, fluoroesters, and fluoroethers. Of course, mixtures of two or more conditioning agents can be used.

The conditioning agent can be any silicone known by those skilled in the art to be useful as a conditioning agent. The silicones suitable for use according to the invention include polyorganosiloxanes that are insoluble in the composition. The silicones may be present in the form of oils, waxes, polymers, or gums. They may be volatile or nonvolatile. The silicones can be selected from polyalkyl siloxanes, polyaryl siloxanes, polyalkyl aryl siloxanes, silicone gums and polymers, and polyorgano siloxanes modified by organofunctional groups, and mixtures thereof. Suitable polyalkyl siloxanes include polydimethyl siloxanes with terminal trimethyl silyl groups or terminal dimethyl silanol groups (dimethiconol) and polyalkyl ($C_1$-$C_{20}$) siloxanes. Suitable polyalkyl aryl siloxanes include polydimethyl methyl phenyl siloxanes and polydimethyl diphenyl siloxanes, linear or branched. The silicone gums suitable for use herein include polydiorganosiloxanes including those having a number-average molecular weight between 200,000 and 1,000,000, used alone or mixed with a solvent. Examples include polymethyl siloxane, polydimethyl siloxane/methyl vinyl siloxane gums, polydimethyl siloxane/diphenyl siloxane, polydimethyl siloxane/phenyl methyl siloxane and polydimethyl siloxane/diphenyl siloxane/methyl vinyl siloxane. Suitable silicone polymers include silicones with a dimethyl/trimethyl siloxane structure and polymers of the trimethyl siloxysilicate type. The organo-modified silicones suitable for use in the invention include silicones such as those previously defined and containing one or more organofunctional groups attached by means of a hydrocarbon radical and grafted siliconated polymers. In one embodiment the silicones are amino functional silicones. The silicones may be used in the form of emulsions, nano-emulsions, or micro-emulsions.

The conditioning agent or agents can be present in an amount from about 0.001% to about 20%, particularly from about 0.01% to about 10%, and even more particularly from about 0.1% to about 3% by weight based on the total weight of the final composition. The personal care/cosmetic compositions of the invention can contain one or more protecting agents in combination with the above-described polymer to prevent or limit the degrading effects of natural physical and/or chemical assaults on the keratinous materials.

The protecting agent can be chosen from hydrosoluble, liposoluble and water-insoluble UV filters, antiradical agents, antioxidants, vitamins and pro-vitamins. The above-described cationic polymer enhances the deposition of these materials onto the hair or skin substrate enhancing protection of hair to UV damage. Organic UV filters (systems that filter out UV rays) can be chosen from among hydrosoluble or liposoluble filters, whether siliconated or nonsiliconated, and mineral oxide particles, the surface of which may be treated. Hydrosoluble organic UV filters may be chosen from para-amino benzoic acid and its salts, anthranilic acid and its salts, salicylic acid and its salts, hydroxy cinnamic acid and its salts, sulfonic derivatives of benzothiazoles, benzimidizoles, benzoxazoles and their salts, sulfonic derivatives of benzophenone and their salts, sulfonic derivatives of benzylidene camphor and their salts, derivatives of benzylidene camphor substituted by a quaternary amine and their salts, derivatives of phthalydene-camphosulfonic acids and their salts, sulfonic derivatives of benzotriazole, and mixtures thereof. Hydrophilic polymers, which have light-protective qualities against UV rays, can be used. These include polymers containing benzylidene camphor and/or benzotriazole groups.

Suitable liposoluble organic UV filters include derivatives of para-aminobenzoic acid, such as the esters or amides of para-aminobenzoic acid; derivatives of salicylic acid; derivatives of benzophenone; derivatives of dibenzoyl methane; derivatives of diphenyl acrylates; derivatives of benzofurans; UV filter polymers containing one or more silico-organic residues; esters of cinnamic acid; derivatives of camphor; derivatives of trianilino-s-triazine; the ethylic ester urocanic acid; benzotriazoles; derivatives of hydroxy phenyl triazine; bis-resorcinol-dialkyl amino triazine; and mixtures thereof. The liposoluble (or lipophilic) organic UV filter can be chosen from octyl salicylate; 4-tert-butyl-4'-methoxy dibenzoyl methane; octocrylene; 4-methoxy cinnamate; 2-ethylhexyl [2-ethylhexyl 4-methoxycinnamate]; and 2-(2H-benzotriazol-2-yl)-4-methyl-6-[2-methyl-3-[1,3,3,3-tetramethyl-1-[(trimethyl silyl)oxy] disiloxanyl]propynyl] phenol. Other UV filters that may be useful are derivatives of benzophenones such as 2-hydroxy-4-methoxy benzophenone-5-sulfonic acid, 2-hydroxy-4-methoxy benzophenone, derivatives of benzalmalonates such as poly dimethyl/methyl (3(4-(2,2-bis-ethoxy carbonyl vinyl)-phenoxy)-propenyl) siloxane, derivatives of benzylidene camphor such as b-b'camphosulfonic [1-4 divinylbenzene] acid and derivatives of benzimidazole such as 2-phenyl-benzimidazol-5-sulfonic acid. Water-insoluble UV filters include various mineral oxides. The mineral oxides may be selected from among titanium oxides, zinc oxides, and cerium oxides. The mineral oxides can be used in the form of ultrafine nanoparticles. For example, the UV filters can include Escalol® HP-610 (dimethylpabamido propyl laurdimonium tosylate and propylene glycol stearate) or Crodasorb HP (polyquaternium 59).

The antioxidants or antiradical agents can be selected from phenols such as BHA (tert-butyl-4-hydroxy anisole), BHT (2,6-di-tert-butyl-p-cresol), TBHQ (tert-butyl hydroquinone), polyphenols such as proanthocyanodic oligomers, flavonoids, hindered amines such as tetra amino piperidine, erythorbic acid, polyamines such as spermine, cysteine, glutathione, superoxide dismutase, and lactoferrin.

The vitamins can be selected from ascorbic acid (vitamin C), vitamin E, vitamin E acetate, vitamin E phosphate, B vitamins such as B3 and B5, vitamin PP, vitamin A, and derivatives thereof. The provitamins can be selected from panthenol and retinol.

The protecting agent can be present in an amount from about 0.001% to about 20% by weight, particularly from about 0.01% to about 10% by weight, and more particularly from 0.1% to about 5% by weight of the total weight of the final composition.

The composition of the invention can contain a fixing agent in combination with the above-described polymer. The fixing agent can be an anionic polymer chosen from polymers containing carboxylic units derived from unsaturated carboxylic mono- or polyacids.

The fixing agent can be an amphoteric polymer chosen from the polymer containing recurring units derived from:
  at least one comonomer containing carboxylic acid units, and
  at least one basic comonomer, such as esters with primary, secondary, tertiary, and quaternary amino substituents of acrylic and methacrylic acids and the product of quaternization of dimethylaminoethyl methacrylate with dimethyl or diethyl sulfate.

The fixing agent can be a nonionic polymer chosen from polyalkyloxazolines; vinyl acetate homopolymers; vinyl acetate and acrylic ester copolymers; vinyl acetate and ethylene copolymers; vinyl acetate and maleic ester copolymers; polyethylene and maleic anhydride copolymers; homopolymers of alkyl acrylates; homopolymers of alkyl methacrylates; copolymers of acrylic esters; copolymers of alkyl acrylates and alkyl methacrylates; copolymers of acrylonitrile and a nonionic monomer chosen from among butadiene and alkyl (meth)acrylates; copolymers of alkyl acrylate and urethane; and polyamides. The fixing agent can be a functionalized or unfunctionalized, silicone or non-silicone polyurethane. The fixing polymer can be a polymer of the grafted silicone type containing a polysiloxane portion and a portion consisting of a nonsilicone organic chain, with one of the two portions forming the main chain of the polymer, and with the other being grafted onto the main chain.

The fixing agent can be present in the composition in a relative weight concentration between about 0.1% to about 10%, for example, from about 0.5% to about 5%.

The personal care/cosmetic composition of the invention can contain an oxidizing agent in combination with the above-described polymer. The oxidizing agent can be chosen from the group of hydrogen peroxide, urea peroxide, alkali metal bromates, ferricyanides, persalts, and redox enzymes, optionally with their respective donor or cofactor. For example, the oxidizing agent can be hydrogen peroxide. The oxidizing agent can be a solution of oxygenated water whose titer varies from 1 to 40 volumes.

The personal care/cosmetic composition of the invention can contain at least one reducing agent in combination with the above-described polymer in amounts from about 0.01% to about 30%, particularly from about 0.05% to about 20% of the total weight of the composition. The reducing agents can be selected from thiols, like cysteine, thioglycolic acid, thiolactic acid, their salts and esters, cysteamine, and its salts or sulfites. In the case of compositions intended for bleaching, ascorbic acid, its salts and its esters, erythorbic acid, its salts and its esters, and sulfinates, like sodium hydroxymethanesulfinate can be used.

The personal care/cosmetic composition of the invention can contain a dye in combination with the above-described polymer. The dye can be selected from the group consisting of neutral acid or cationic nitrobenzene dyes, neutral acid or cationic azo dyes, quinone dyes, neutral, acid or cationic anthraquinone dyes, azine dyes, triarylmethane dyes, indoamine dyes and natural dyes. The dye or dyes can be present in a concentration from about 0.001% to about 20%, and particularly from about 0.005% to about 10% based on the total weight of the composition.

In addition, the personal care/cosmetic compositions can include at least one surfactant in combination with the above-described polymer. The surfactant can be present in an amount from about 0.1% to about 60%, particularly from about 1% to about 40%, and more particularly from about 5% to about 30% by weight based on the total weight of the composition. The surfactant may be chosen from among anionic, amphoteric, or non-ionic surfactants, or mixtures of them known to be useful in personal care/cosmetic compositions.

One or more suitable thickeners or viscosity increasing agents may be included in combination with the above-described polymer in the personal care/cosmetic compositions of the invention. Suitable thickeners and/or viscosity increasing agents include: Acetamide MEA; Acrylamide/Ethalkonium Chloride Acrylate Copolymer; Acrylamide/Ethyltrimonium Chloride Acrylate/Ethalkonium Chloride Acrylate Copolymer; Acrylamides Copolymer; Acrylamide/Sodium Acrylate Copolymer; Acrylamide/Sodium Acryloyldimethyltaurate Copolymer; Acrylates/Acetoacetoxyethyl Methacrylate Copolymer; Acrylates/Beheneth-25 Methacrylate Copolymer; Acrylates/C10-30 Alkyl Acrylate Crosspolymer; Acrylates/Ceteth-20 Itaconate Copolymer; Acrylates/Ceteth-20 Methacrylate Copolymer; Acrylates/Laureth-25 Methacrylate Copolymer; Acrylates/Palmeth-25 Acrylate Copolymer; Acrylates/Palmeth-25 Itaconate Copolymer; Acrylates/Steareth-50 Acrylate Copolymer; Acrylates/Steareth-20 Itaconate Copolymer; Acrylates/Steareth-20 Methacrylate Copolymer; Acrylates/Stearyl Methacrylate Copolymer; Acrylates/Vinyl Isodecanoate Crosspolymer; Acrylic Acid/Acrylonitrogens Copolymer; Adipic Acid/Methyl DEA Crosspolymer; Agar; Agarose; *Alcaligenes* Polysaccharides; Algin; Alginic Acid; Almondamide DEA; Almondamidopropyl Betaine; Aluminum/Magnesium Hydroxide Stearate; Ammonium Acrylates/Acrylonitrogens Copolymer; Ammonium Acrylates Copolymer; Ammonium Acryloyldimethyltaurate/Vinyl Formamide Copolymer; Ammonium Acryloyldimethyltaurate/VP Copolymer; Ammonium Alginate, Ammonium Chloride; Ammonium Polyacryloyldimethyl Taurate; Ammonium Sulfate;

Amylopectin; Apricotamide DEA; Apricotamidopropyl Betaine; Arachidyl Alcohol; Arachidyl Glycol; *Arachis Hypogaea* (Peanut) Flour; Ascorbyl Methylsilanol Pectinate; *Astragalus* Gummifer Gum; Attapulgite; *Avena Sativa* (Oat) Kernel Flour; Avocadamide DEA; Avocadamidopropyl Betaine, Azelamide MEA; Babassuamide DEA; Babassuamide MEA; Babassuamidopropyl Betaine; Behenamide DEA; Behenamide MEA, Behenamidopropyl Betaine; Behenyl Betaine; Bentonite; Butoxy Chitosan, *Caesalpinia Spinosa* Gum; Calcium Alginate; Calcium Carboxymethyl Cellulose; Calcium Carrageenan; Calcium Chloride; Calcium Potassium Carbomer; Calcium Starch Octenylsuccinate; C20-40 Alkyl Stearate; Canolamidopropyl Betaine; Capramide DEA; Capryl/Capramidopropyl Betaine; Carbomer; Carboxybutyl Chitosan; Carboxymethyl Cellulose Acetate Butyrate; Carboxymethyl Chitin; Carboxymethyl Chitosan; Carboxymethyl Dextran; Carboxymethyl Hydroxyethylcellulose; Carboxymethyl Hydroxypropyl Guar; Carnitine; Cellulose Acetate Propionate Carboxylate; Cellulose Gum; *Ceratonia Siliqua* Gum; Cetearyl Alcohol; Cetyl Alcohol; Cetyl Babassuate; Cetyl Betaine; Cetyl Glycol; Cetyl Hydroxyethylcellulose; Chimyl Alcohol; Cholesterol/HDI/Pullulan Copolymer; Cholesteryl Hexyl Dicarbamate Pullulan; *Citrus Aurantium Dulcis* (Orange) Peel Extract; Cocamide DEA; Cocamide MEA; Cocamide MIPA; Cocamidoethyl Betaine; Cocamidopropyl Betaine; Cocamidopropyl Hydroxysultaine; Coco-Betaine; Coco-Hydroxysultaine; Coconut Alcohol; Coco/Oleamidopropyl Betaine; Coco-Sultaine; Cocoyl Sarcosinamide DEA; Cornamide/Cocamide DEA; Cornamide DEA; Croscarmellose; Crosslinked *Bacillus*/Glucose/Sodium Glutamate Ferment; *Cyamopsis Tetragonoloba* (Guar) Gum; Decyl Alcohol; Decyl Betaine; Dehydroxanthan Gum; Dextrin; Dibenzylidene Sorbitol; Diethanolaminooleamide DEA; Diglycol/CHDM/Isophthalates/SIP Copolymer; Dihydroabietyl Behenate; Dihydrogenated Tallow Benzylmonium Hectorite; Dihydroxyaluminum Aminoacetate; Dimethicone/PEG-10 Crosspolymer; Dimethicone/PEG-15 Crosspolymer; Dimethicone Propyl PG-Betaine; Dimethylacrylamide/Acrylic Acid/Polystyrene Ethyl Methacrylate Copolymer; Dimethylacrylamide/Sodium Acryloyldimethyltaurate Crosspolymer; Disteareth-100 IPDI; DMAPA Acrylates/Acrylic Acid/Acrylonitrogens Copolymer; Erucamidopropyl Hydroxysultaine; Ethylene/Sodium Acrylate Copolymer; Gelatin; Gellan Gum; Glyceryl Alginate; *Glycine Soja* (Soybean) Flour; Guar Hydroxypropyltrimonium Chloride; Hectorite; Hyaluronic Acid; Hydrated Silica; Hydrogenated Potato Starch; Hydrogenated Tallow; Hydrogenated Tallowamide DEA; Hydrogenated Tallow Betaine; Hydroxybutyl Methylcellulose; Hydroxyethyl Acrylate/Sodium Acryloyldimethyl Taurate Copolymer; Hydroxyethylcellulose; Hydroxyethyl Chitosan; Hydroxyethyl cellulose; Hydroxyethyl Stearamide-MIPA; Hydroxylauryl/Hydroxymyristyl Betaine; Hydroxypropylcellulose; Hydroxypropyl Chitosan; Hydroxypropyl Ethylenediamine Carbomer; Hydroxypropyl Guar; Hydroxypropyl Methylcellulose; Hydroxypropyl Methylcellulose Stearoxy Ether; Hydroxypropyl Starch; Hydroxypropyl Starch Phosphate; Hydroxypropyl Xanthan Gum; Hydroxystearamide MEA; Isobutylene/Sodium Maleate Copolymer; Isostearamide DEA; Isostearamide MEA; Isostearamide MIPA; Isostearamidopropyl Betaine; Lactamide MEA; Lanolinamide DEA; Lauramide DEA; Lauramide MEA; Lauramide MIPA; Lauramide/Myristamide DEA; Lauramidopropyl Betaine; Lauramidopropyl Hydroxysultaine; Laurimino Bispropanediol; Lauryl Alcohol; Lauryl Betaine; Lauryl Hydroxysultaine; Lauryl/Myristyl Glycol Hydroxypropyl Ether; Lauryl Sultaine; Lecithinamide DEA; Linoleamide DEA; Linoleamide MEA; Linoleamide MIPA; Lithium Magnesium Silicate; Lithium Magnesium Sodium Silicate; *Macrocystis Pyrifera* (Kelp); Magnesium Alginate; Magnesium/Aluminum/Hydroxide/Carbonate; Magnesium Aluminum Silicate; Magnesium Silicate; Magnesium Trisilicate; Methoxy PEG-22/Dodecyl Glycol Copolymer; Methylcellulose; Methyl Ethylcellulose; Methyl Hydroxyethylcellulose; Microcrystalline Cellulose; Milkamidopropyl Betaine; Minkamide DEA; Minkamidopropyl Betaine; MIPA-Myristate; Montmorillonite; Moroccan Lava Clay; Myristamide DEA; Myristamide MEA; Myristamide MIPA; Myristamidopropyl Betaine; Myristamidopropyl Hydroxysultaine; Myristyl Alcohol; Myristyl Betaine; Natto Gum; Nonoxynyl Hydroxyethylcellulose; Oatamide MEA; Oatamidopropyl Betaine; Octacosanyl Glycol Isostearate; Octadecene/MA Copolymer; Oleamide DEA; Oleamide MEA; Oleamide MIPA; Oleamidopropyl Betaine; Oleamidopropyl Hydroxysultaine; Oleyl Betaine; Olivamide DEA; Olivamidopropyl Betaine; Oliveamide MEA; Palmamide DEA; Palmamide MEA; Palmamide MIPA; Palmamidopropyl Betaine; Palmitamide DEA; Palmitamide MEA; Palmitamidopropyl Betaine; Palm Kernel Alcohol; Palm Kernelamide DEA; Palm Kernelamide MEA; Palm Kernelamide MIPA; Palm Kernelamidopropyl Betaine; Peanutamide MEA; Peanutamide MIPA; Pectin; PEG-800; PEG-Crosspolymer; PEG-150/Decyl Alcohol/SMDI Copolymer; PEG-175 Diisostearate; PEG-190 Distearate; PEG-15 Glyceryl Tristearate; PEG-140 Glyceryl Tristearate; PEG-240/HDI Copolymer Bis-Decyltetradeceth-20 Ether; PEG-100/IPDI Copolymer; PEG-180/Laureth-50/TMMG Copolymer; PEG-10/Lauryl Dimethicone Crosspolymer; PEG-15/Lauryl Dimethicone Crosspolymer; PEG-2M; PEG-5M; PEG-7M; PEG-9M; PEG-14M; PEG-20M; PEG-23M; PEG-25M; PEG-45M; PEG-65M; PEG-90M; PEG-115M; PEG-160M; PEG-180M; PEG-120 Methyl Glucose Trioleate; PEG-180/Octoxynol-40/TMMG Copolymer; PEG-150 Pentaerythrityl Tetrastearate; PEG-4 Rapeseedamide; PEG-150/Stearyl Alcohol/SMDI Copolymer; *Phaseolus Angularis* Seed Powder; *Polianthes Tuberosa* Extract; Polyacrylate-3; Polyacrylic Acid; Polycyclopentadiene; Polyether-1; Polyethylene/Isopropyl Maleate/MA Copolyol; Polyglyceryl-3 Disiloxane Dimethicone; Polyglyceryl-3 Polydimethylsiloxyethyl Dimethicone; Polymethacrylic Acid; Polyquaternium-52; Polyvinyl Alcohol; Potassium Alginate; Potassium Aluminum Polyacrylate; Potassium Carbomer; Potassium Carrageenan; Potassium Chloride; Potassium Palmate; Potassium Polyacrylate; Potassium Sulfate; Potato Starch Modified; PPG-2 Cocamide; PPG-1 Hydroxyethyl Caprylamide; PPG-2 Hydroxyethyl Cocamide; PPG-2 Hydroxyethyl Coco/Isostearamide; PPG-3 Hydroxyethyl Soyamide; PPG-14 Laureth-60 Hexyl Dicarbamate; PPG-14 Laureth-60 Isophoryl Dicarbamate; PPG-14 Palmeth-60 Hexyl Dicarbamate; Propylene Glycol Alginate; PVP/Decene Copolymer; PVP Montmorillonite; *Pyrus Cydonia* Seed; *Pyrus Malus* (Apple) Fiber; Rhizobian Gum; Ricebranamide DEA; Ricinoleamide DEA; Ricinoleamide MEA; Ricinoleamide MIPA; Ricinoleamidopropyl Betaine; Ricinoleic Acid/Adipic Acid/AEEA Copolymer; *Rosa Multiflora* Flower Wax; *Sclerotium* Gum; Sesamide DEA; Sesamidopropyl Betaine; Sodium Acrylate/Acryloyldimethyl Taurate Copolymer; Sodium Acrylates/Acrolein Copolymer; Sodium Acrylates/Acrylonitrogens Copolymer; Sodium Acrylates Copolymer; Sodium Acrylates Crosspolymer; Sodium Acrylate/Sodium Acrylamidomethylpropane Sulfonate Copolymer; Sodium Acrylates/Vinyl Isodecanoate Crosspolymer; Sodium Acrylate/Vinyl Alcohol Copolymer;

Sodium Carbomer; Sodium Carboxymethyl Chitin; Sodium Carboxymethyl Dextran; Sodium Carboxymethyl Beta-Glucan; Sodium Carboxymethyl Starch; Sodium Carrageenan; Sodium Cellulose Sulfate; Sodium Chloride; Sodium Cyclodextrin Sulfate; Sodium Hydroxypropyl Starch Phosphate; Sodium Isooctylene/MA Copolymer; Sodium Magnesium Fluorosilicate; Sodium Oleate; Sodium Palmitate; Sodium Palm Kernelate; Sodium Polyacrylate; Sodium Polyacrylate Starch; Sodium Polyacryloyldimethyl Taurate; Sodium Polygamma-Glutamate; Sodium Polymethacrylate; Sodium Polystyrene Sulfonate; Sodium Silicoaluminate; Sodium Starch Octenylsuccinate; Sodium Stearate; Sodium Stearoxy PG-Hydroxyethylcellulose Sulfonate; Sodium Styrene/Acrylates Copolymer; Sodium Sulfate; Sodium Tallowate; Sodium Tauride Acrylates/Acrylic Acid/Acrylonitrogens Copolymer; Sodium Tocopheryl Phosphate; *Solanum Tuberosum* (Potato) Starch; Soyamide DEA; Soyamidopropyl Betaine; Starch/Acrylates/Acrylamide Copolymer; Starch Hydroxypropyltrimonium Chloride; Stearamide AMP; Stearamide DEA; Stearamide DEA-Distearate; Stearamide DIBA-Stearate; Stearamide MEA; Stearamide MEA-Stearate; Stearamide MIPA; Stearamidopropyl Betaine; Steareth-60 Cetyl Ether; Steareth-100/PEG-136/HDI Copolymer; Stearyl Alcohol; Stearyl Betaine; *Sterculia Urens* Gum; Synthetic Fluorphlogopite; Tallamide DEA; Tallow Alcohol; Tallowamide DEA; Tallowamide MEA; Tallowamidopropyl Betaine; Tallowamidopropyl Hydroxysultaine; Tallowamine Oxide; Tallow Betaine; Tallow Dihydroxyethyl Betaine; Tamarindus Indica Seed Gum; Tapioca Starch; TEA-Alginate; TEA-Carbomer; TEA-Hydrochloride; Trideceth-2 Carboxamide MEA; Tridecyl Alcohol; Triethylene Glycol Dibenzoate; Trimethyl Pentanol Hydroxyethyl Ether; *Triticum Vulgare* (Wheat) Germ Powder; *Triticum Vulgare* (Wheat) Kernel Flour; *Triticum Vulgare* (Wheat) Starch; Tromethamine Acrylates/Acrylonitrogens Copolymer; Tromethamine Magnesium Aluminum Silicate; Undecyl Alcohol; Undecylenamide DEA; Undecylenamide MEA; Undecylenamidopropyl Betaine; Welan Gum; Wheat Germamide DEA; Wheat Germamidopropyl Betaine; Xanthan Gum; Yeast Beta-Glucan; Yeast Polysaccharides and *Zea Mays* (Corn) Starch.

In one such embodiment, the thickeners or viscosity increasing agents include carbomers, Aculyn™ and Stabileze®, e.g., crosslinked acrylic acid, crosslinked poly (methylvinyl ether/maleic anhydride) copolymer, acrylamides, carboxymethyl cellulose, and the like.

The personal care/cosmetic composition of the invention can contain at least one amphoteric polymer or a cationic polymer in combination with the above-described polymer. The cationic or amphoteric polymer or polymers can be present in an amount from about 0.01% to about 10%, particularly from about 0.05% to about 5%, and more particularly from about 0.1% to about 3% by weight of the total weight of the composition.

For some embodiments, it may be preferred to add one or more preservatives and/or antimicrobial agents, such as, but not limited to, benzoic acid, sorbic acid, dehydroacetic acid, piroctone olamine, DMDM hydantoin, IPBC, triclosan, bronopol, formaldehyde, isothiazolinones, nitrates/nitrites, parabens, phenoxyethanol, potassium sorbate, sodium benzoate, sulphites, and sulphur dioxide. Combinations of preservatives may be used.

In other embodiments it may be desirable to incorporate preservative boosters/solvents, select examples of which include caprylyl glycol, hexylene glycol, pentylene glycol, ethylhexylglycerin, caprylhydroxamic acid, and glyceryl caprylate.

In other embodiments it may be desirable to include one or more other ingredients, such as synthetic and natural oils and waxes. The synthetic oils include polyolefins, e.g., poly-α-olefins such as polybutenes, polyisobutenes and polydecenes. The polyolefins can be hydrogenated. The mineral oils suitable for use in the compositions of the invention include hexadecane and oil of paraffin. Suitable animal and vegetable oils include sunflower, corn, soy, avocado, jojoba, squash, raisin seed, sesame seed, walnut oils, fish oils, glycerol tricaprocaprylate, Purcellin oil or liquid jojoba. Suitable natural or synthetic oils include *eucalyptus*, lavender, vetiver, *litsea cubeba*, lemon, sandalwood, rosemary, chamomile, savory, nutmeg, cinnamon, hyssop, caraway, orange, geranium, cade, and bergamot. Suitable natural and synthetic waxes include carnauba wax, candelila wax, alfa wax, paraffin wax, ozokerite wax, vegetable waxes such as olive wax, rice wax, hydrogenated jojoba wax, absolute flower waxes such as black currant flower wax, animal waxes such as bees wax, modified bees wax (cerabellina), marine waxes and polyolefin waxes such as polyethylene wax.

The personal care/cosmetic compositions may be used to wash and treat keratinous material such as hair, skin, eyelashes, eyebrows, fingernails, lips, and hairy skin. The invention provides a method for treating keratinous material including the skin or hair, by applying to skin or keratinous materials a personal care/cosmetic composition as described above, and then eventually rinsing it with water. Accordingly, the method makes it possible to maintain the hairstyle, treatment, care, washing, or make-up removal of the skin, the hair, and any other keratinous material.

The personal care/cosmetic compositions described herein are useful in personal care/cosmetic products, including, but not limited to, gels, lotions, glazes, glues, mousses, sprays, fixatives, shampoos, conditioners, 2-in-1 shampoos, temporary hair dyes, semi-permanent hair dyes, permanent hair dyes, straighteners, permanent waves, relaxers, creams, putties, waxes, pomades, moisturizers, mascaras, lip balms and foam enhancers. The personal care/cosmetic compositions can be detergent compositions such as shampoos, bath gels, and bubble baths. In this mode, the compositions will comprise a generally aqueous washing base. The surfactant or surfactants that form the washing base may be chosen alone or in blends, from known anionic, amphoteric, or non-ionic surfactants. The quantity and quality of the washing base must be sufficient to impart a satisfactory foaming and/or detergent value to the final composition. The washing base can be from about 4% to about 50% by weight, particularly from about 6% to about 35% by weight, and even more particularly from about 8% to about 25% by weight of the total weight of the final composition. The personal care/cosmetic compositions may also take the form of after-shampoo compositions, to be rinsed off or not, for permanents, straightening, waving, dyeing, or bleaching, or the form of rinse compositions to be applied before or after dyeing, bleaching, permanents, straightening, relaxing, waving or even between the two stages of a permanent or straightening process. The personal care/cosmetic compositions may also take the form of skin-washing compositions, and particularly in the form of solutions or gels for the bath or shower, or of make-up removal products. The personal care/cosmetic compositions may also be in the form of aqueous or hydro-alcoholic solutions for skin and/or hair care.

The pH of the composition applied to the keratinous material is generally between 2 and 12. In one embodiment, the pH is from about 3 to about 8, and may be adjusted to the desired value by means of acidifying or alkalinizing agents that are well known in the state of the art. Thus, the composition of the invention can contain at least one alkalizing or acidifying agent in amounts from about 0.01% to about 30% based on the total weight of the composition.

The alkalizing agent can be chosen from ammonia, alkali hydroxides, alkali carbonates, alkanolamines, like mono-, di- and triethanolamines, as well as their derivatives, hydroxyalkylamines and ethoxylated and/or propoxylated ethylenediamines, unsubstituted and substituted propylenediamines.

The acidifying agent can be chosen from mineral or organic acids, like hydrochloric acid, orthophosphoric acid, carboxylic acids like tartaric acid, citric acid, or lactic acid, or sulfonic acids, and the like.

The personal care/cosmetic compositions of the invention may include a physiological and cosmetically acceptable medium. Such medium may consist exclusively of water, a cosmetically acceptable solvent, or a blend of water and a cosmetically acceptable solvent, such as a lower alcohol composed of $C_1$ to $C_4$, such as ethanol, isopropanol, t-butanol, n-butanol, alkylene glycols such as propylene glycol, and glycol ethers. Alternatively, the personal care/cosmetic compositions can be anhydrous.

Generally, personal care/cosmetic compositions can be prepared by simple mixing procedures well known in the art.

The polymers containing an amic acid or an imide group can be prepared according to the examples set out below. The examples are presented for purposes of demonstrating, but not limiting, the preparation of the compounds and compositions of this invention.

EXAMPLES

Example 1

General Protocol for Heterogeneous MVE/AVE/MAh Terpolymer Synthesis

TABLE 1

Synthesized examples of MVE/AVE/MAh Terpolymers via Homogeneous and/or Heterogeneous Process

| Sample # | P(MVE/AVE/MAh) Molar Ratio | Heterogeneous Process | Homogeneous Process |
|---|---|---|---|
| 1 | 45/5/50 | Yes | Yes |
| 2 | 40/10/50 | Yes | Yes |
| 3 | 35/15/50 | Yes | Yes |
| 4 | 20/30/50 | Yes | Yes |
| 5 | 10/40/50 | Yes | Yes |
| 6 | 5/45/50 | Yes | Yes |

A 1-L Buchi reactor was charged with solvent mixture, ethyl acetate/cyclohexane (EA:CY, 1:1 wt. ratio) and alkyl vinyl ether (AVE) then sealed, agitation initiated, and purged with nitrogen five times. Following this, methyl vinyl ether (MVE) was charged to the reactor, and the reactor was heated to 70° C., and then maleic anhydride (MAh) was added for the next 3 hours (unless otherwise noted). At this time a stock solution (1.5% active) was prepared containing decanoyl peroxide (DCP) (initiator) and additional solvent blend. Fifteen minutes after the MAh feed was begin, the initiator solution fed was started to the reactor at a constant rate and then stopped once MAh feed was complete (which could take up to three hours or more). The polymerization temperature (70° C.) was maintained for an additional 1 hour after initiator feed was stopped, and then the reactor was cooled to room temperature (about 25° C.) before discharging the polymer mixture (about 23% solids). Polymer mixture was hood dried overnight in a glass tray followed by vacuum drying process at 65° C. (4 h).

As an example, for the synthesis of Sample #1 (see Table 1) 250 g of cylohexane:ethyl acetate (1:1 wt) solvent mixture, 25 g of methyl vinyl ether (MVE), 11 g of dodecyl vinyl ether (DDVE), 47 g of maleic anhydride (MAh), and 0.41 g of decanoyl peroxide (DCP) were used to create following the detailed general procedure a polymer having a chemical composition: 45 mol % MVE, 50 mol % MAh, and 5 mole % DDVE.

Example 2

General Protocol for Homogeneous MVE/AVE/MAh Terpolymer Synthesis

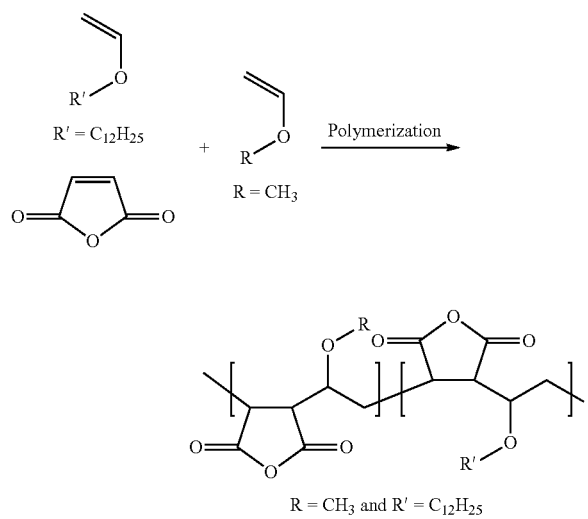

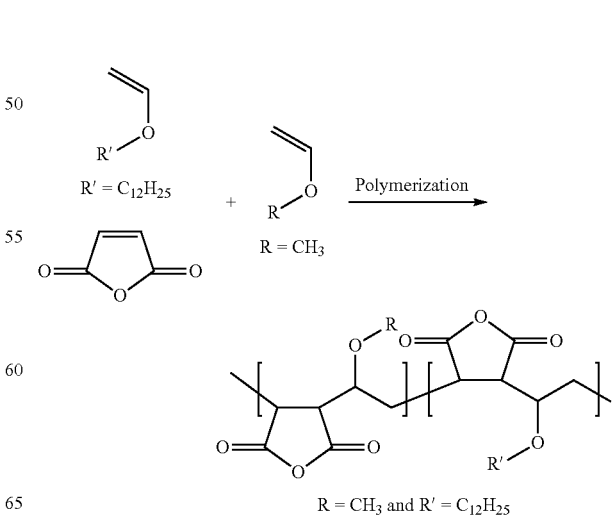

A 1-L Buchi reactor was charged with solvent, methyl ethyl ketone (MEK) and alkyl vinyl ether (AVE) then sealed, agitation initiated, and purged with nitrogen five times. Following this, methyl vinyl ether (MVE) was charged to the reactor, and the reactor was heated to 70° C., and then maleic anhydride (MAh) was added for the next 3 hours (unless otherwise noted). At this time a stock solution (1.5% solids) was prepared containing decanoyl peroxide (DCP) (initiator) and additional solvent blend. Fifteen minutes after the MAh feed was begun, the initiator solution was fed to the reactor at a constant rate and then stopped once MAh feed was complete (which could take up to three hours or more).

The polymerization temperature (70° C.) was maintained for an additional 1 hour, and then the reactor was cooled to room temperature (about 25° C.) before discharging the polymer mixture (about 23% solids). Polymer mixture was hood dried overnight in a glass tray followed by vacuum drying at 65° C. (4 h).

Example 3

Heterogenous Process for Modification with K-Taurine of MVE/AVE/MAh Terpolymers

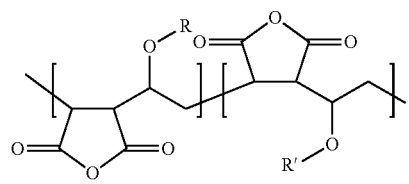

R = CH$_3$ and R' = C$_{12}$H$_{25}$

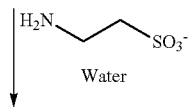

Water

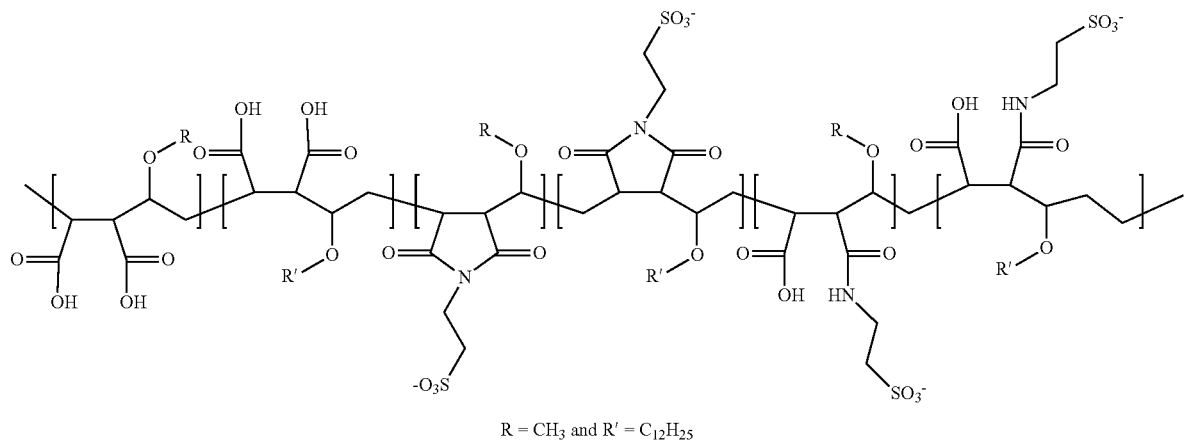

R = CH$_3$ and R' = C$_{12}$H$_{25}$

A 25% solids K-Taurine solution made up of 56 g KOH, 125 g of K-Taurine and 471 g of DI water was prepared and used for modification of MVE/AVE/MAh terpolymer.

For modification of the terpolymer, the polymer (5 g) was mixed with K-taurine solution and additional water (to make up a 20-22% solids mixture) and the heterogeneous mixture placed in a 100 mL high pressure bomb and sealed under nitrogen. Two-step heating process was employed, first for the first 10 hrs the mixture was heated at 100° C., and then for the next 14 hrs, temperature was raised to 140° C. Following this high temperature process, mixture was cooled to room temperature and then removed from the container. A viscous brown homogeneous mixture was obtained. Analytical work (FTIR, NMR) demonstrated the presence of amide, imide, diacid and corresponding salt variants.

Example 4

Heterogenous Process for Modification with Ethanol/Amine of MVE/AVE/MAh Terpolymers

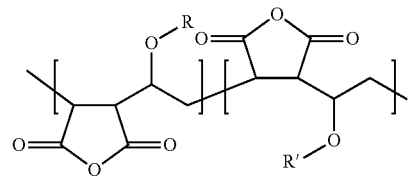

R = CH$_3$ and R' = C$_{12}$H$_{25}$

Amine
Ethanol ↓

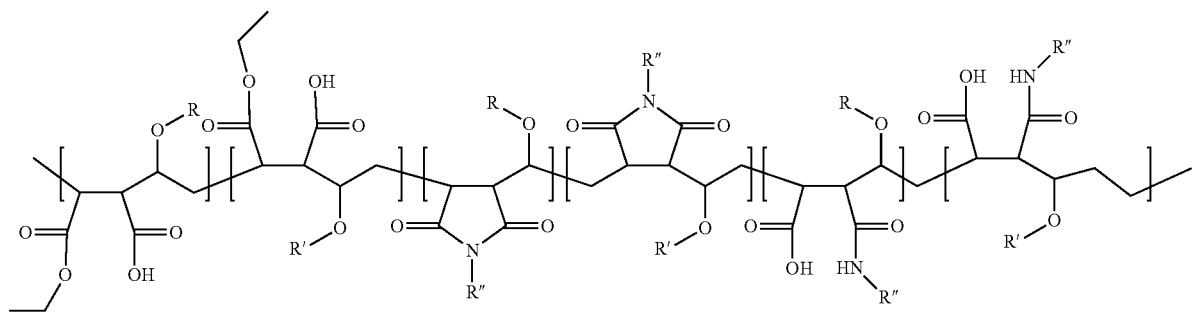

R = CH$_3$ and R' = C$_{12}$H$_{25}$; R'' = C$_8$H$_{17}$ or C$_{12}$H$_{25}$ or C$_{16}$H$_{33}$ A premix of the required amount of amine was prepared in the required quantity of ethanol to yield a 20% solution. For the modification of the terpolymer, the starting material is placed in a high pressure reactor (such as a high pressure bomb for small scale batches) and the premixed amine-ethanol solution is added, then the polymer mixture is vigorously mixed and purged with nitrogen for several times and then reactor is sealed under nitrogen and heated up to 110° C. At that temperature polymer mixture is kept under constant mixing for 1 hr and then temperature is raised to 125° C. and maintained for an additional 8 hrs. Following this step, reaction mixture is cooled to room temperature, reactor is discharged and a homogeneous polymer mixture is obtained. Analytical work (FTIR, NMR) demonstrated the presence of functional groups on polymer backbone such as amide, imide, diester and half ester.

Example 5

Homogeneous Process for Modification with Amine of MVE/AVE/MAh Terpolymers

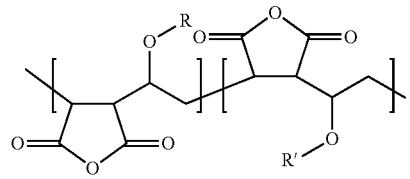

R = CH$_3$ and R' = C$_{12}$H$_{25}$

Amine ↓

-continued

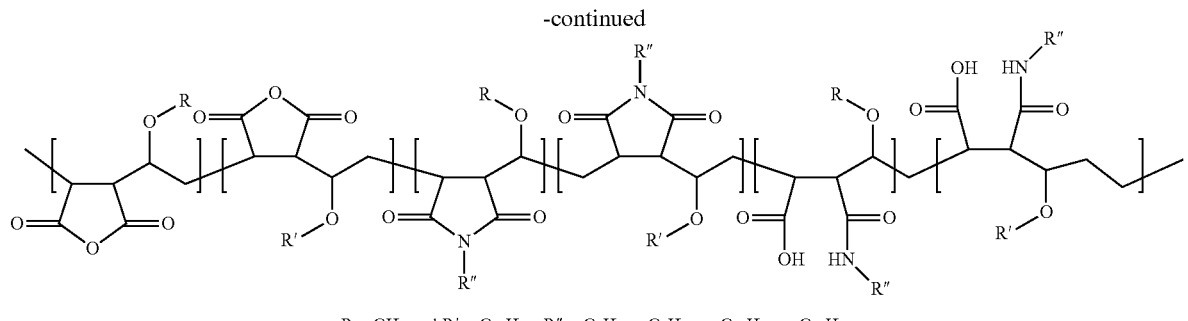

R = CH₃ and R' = C₁₂H₂₅; R'' = C₄H₉ or C₈H₁₇ or C₁₂H₂₅ or C₁₆H₃₃

The terpolymer was dissolved in the required quantity of ethyl acetate to yield a 20% solution, then place the terpolymer solution in a kettle reactor and under nitrogen and vigorous agitation feed dropwise a solution of the amine dispersed in ethyl acetate (30% dilution) at RT for 2-3 hrs. After the amine feed is completed the reaction mixture temperature was raised to 50° C. and maintained under mixing for an additional 8 hrs. Following this step, reaction mixture discharged from the reactor is discharged and polymer dried first in the hood overnight then in a vacuum oven at 40° C. for 6 h. The obtained solid material is grinded and an off-white powder was obtained. Analytical work (FTIR, NMR) demonstrated the presence of the expected functional groups on polymer backbone such as amide, imide, anhydride, disalts, and diacids.

While a number of embodiments of this invention have been represented, it was apparent that the basic construction may be altered to provide other embodiments that utilize the invention without departing from the spirit and scope of the invention. All such modifications and variations are intended to be included within the scope of the invention as defined in the appended claims rather than the specific embodiments that have been presented by way of example.

We claim:

1. The polymer comprising:
   (a) a first repeating unit selected from the group consisting of:

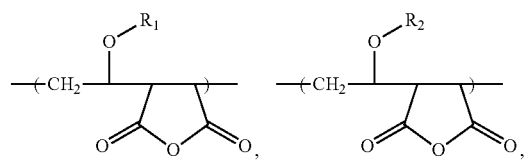

and combinations thereof, and
   (b) a second repeating unit selected from the group consisting of:

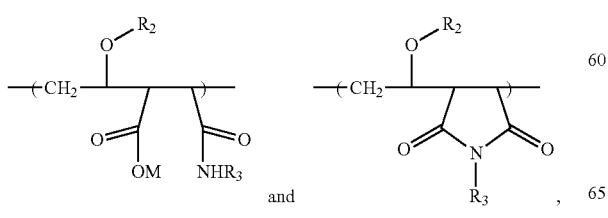

and combinations thereof, wherein $R_1$ is a $C_1$-$C_7$ alkyl group, $R_2$ is a $C_8$-$C_{30}$ alkyl group, $R_3$ is a $C_1$-$C_{30}$ alkyl group, and M is selected from the group consisting of hydrogen, alkali metals, alkaline earth metals, ammonium salts, and combinations thereof.

2. The polymer according to claim 1, further comprising a repeating unit selected from the group consisting of:

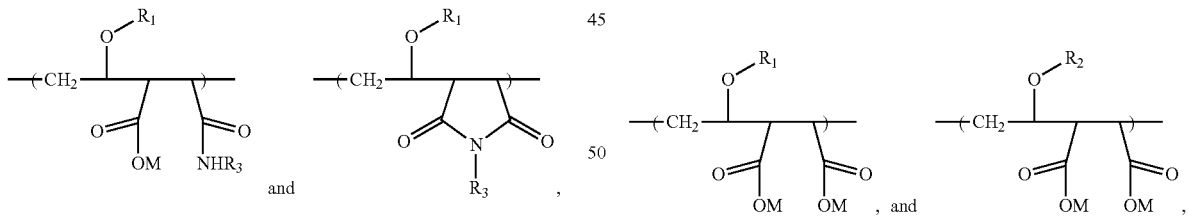

and combinations thereof; wherein $R_1$ is a $C_1$-$C_7$ alkyl group, $R_2$ is a $C_8$-$C_{30}$ alkyl group, and M is selected from the group consisting of hydrogen, alkali metals, alkaline earth metals, ammonium salts, and combinations thereof.

3. The polymer according to claim 2, wherein $R_1$ is $CH_3$, $R_2$ is $C_{12}H_{25}$, $R_3$ is selected from the group consisting of $C_4H_9$, $C_8H_{17}$, $C_{12}H_{25}$, and $C_{16}H_{33}$, and M is H or Na.

4. The polymer according to claim 2, wherein the polymer is represented by the following structure:

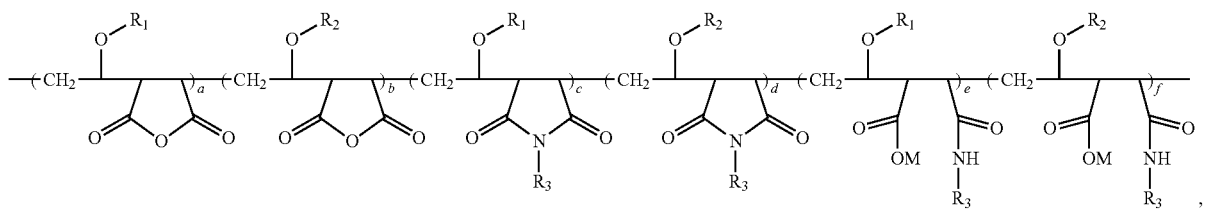

wherein $R_1$ is a $C_1$-$C_7$ alkyl group, $R_2$ is a $C_8$-$C_{30}$ alkyl group, $R_3$ is a $C_1$-$C_{30}$ alkyl group, and M is selected from the group consisting of hydrogen, alkali metals, alkaline earth metals, ammonium salts, and combinations thereof, wherein a, b, c, d, e, and f are molar amounts, the sum of which equals 100%, providing that c and d are not both zero at the same time.

5. The polymer according to claim 4, wherein the polymer is represented by the following structure:

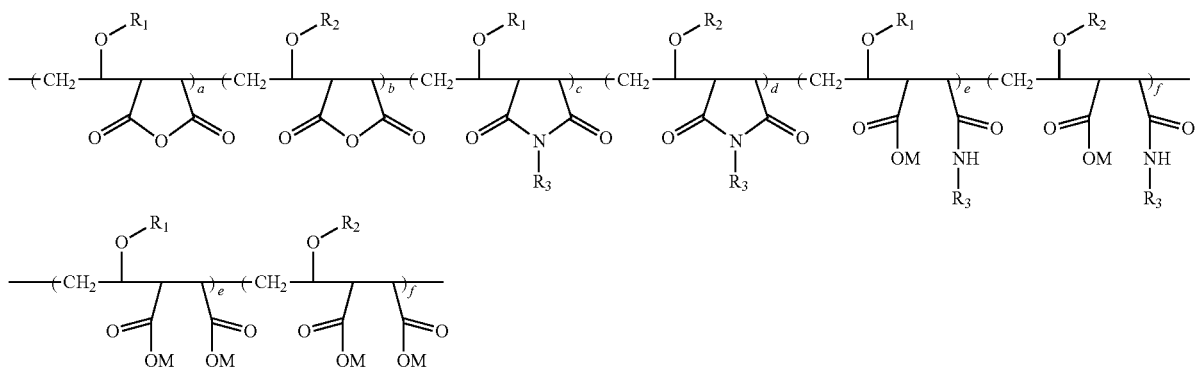

wherein $R_1$ is a $C_1$-$C_7$ alkyl group, $R_2$ is a $C_8$-$C_{30}$ alkyl group, $R_3$ is a $C_1$-$C_{30}$ alkyl group, and M is selected from the group consisting of hydrogen, alkali metals, alkaline earth metals, ammonium salts, and combinations thereof, wherein a, b, c, d, e, and f are molar amounts, the sum of which equals 100%, providing that c and d are not both zero at the same time and e and f are not both zero at the same time.

6. The polymer according to claim 4, selected from the group consisting of:

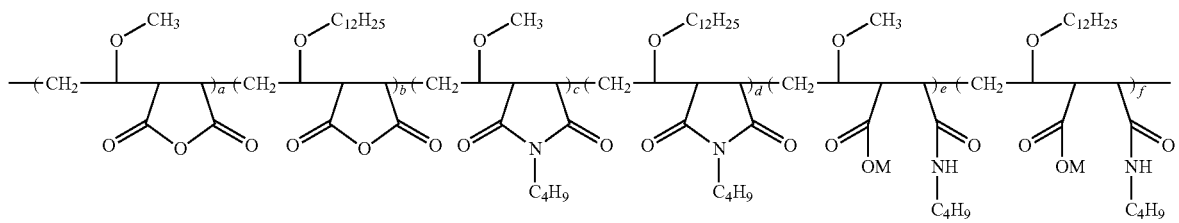

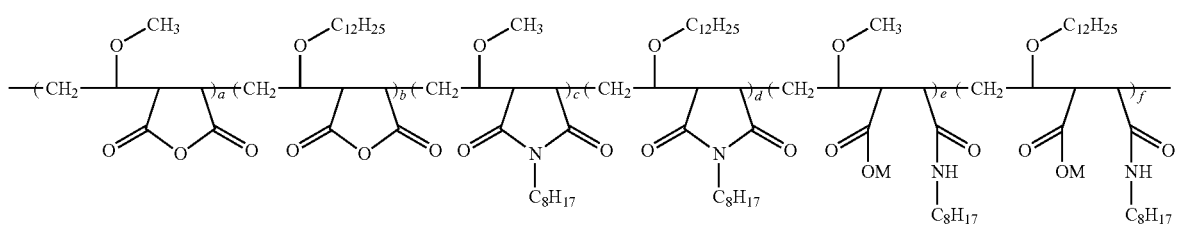

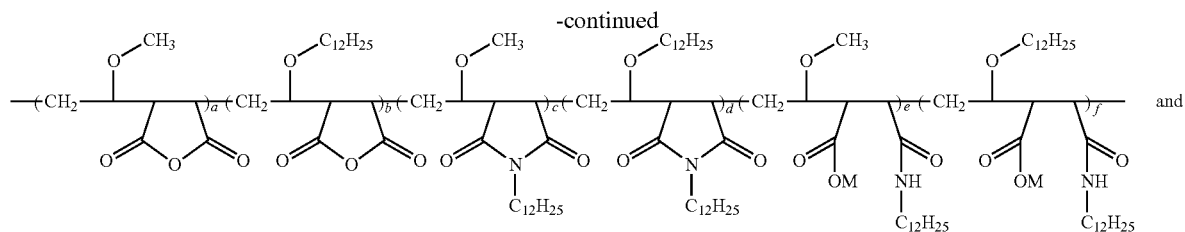

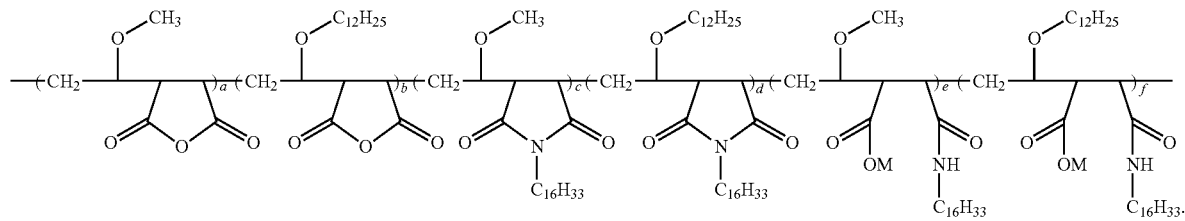

7. A composition comprising a polymer comprising: (a) maleic anhydride, (b) a first $C_1$-$C_7$ alkyl vinyl ether monomer, and (c) a second $C_8$-$C_{30}$ alkyl vinyl ether monomer, wherein the polymer contains an amic acid or an imide group.

8. The composition according to claim 7, comprising:
(a) a first repeating unit selected from the group consisting of:

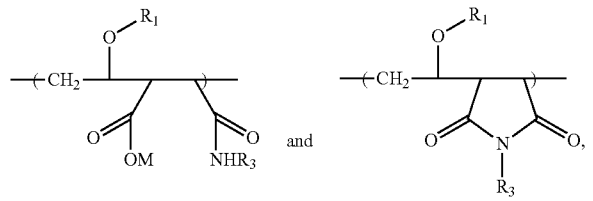

and combinations thereof, and
(b) a second repeating unit selected from the group consisting of:

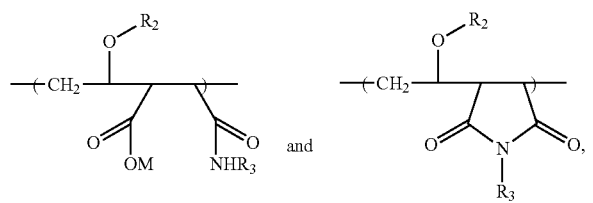

and combinations thereof, wherein $R_1$ is a $C_1$-$C_7$ alkyl group, $R_2$ is a $C_8$-$C_{30}$ alkyl group, $R_3$ is a $C_1$-$C_{30}$ alkyl group, and M is selected from the group consisting of hydrogen, alkali metals, alkaline earth metals, ammonium salts, and combinations thereof.

9. The composition according to claim 8, further comprising a repeating unit selected from the group consisting of:

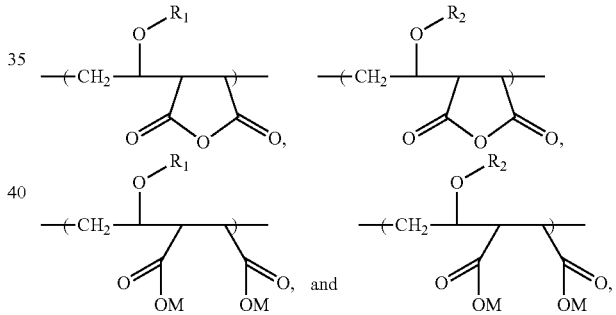

and combinations thereof; wherein $R_1$ is a $C_1$-$C_7$ alkyl group, $R_2$ is a $C_8$-$C_{30}$ alkyl group, and M is selected from the group consisting of hydrogen, alkali metals alkaline earth metals, ammonium salts, and combinations thereof.

10. The composition according to claim 9, wherein $R_1$ is $CH_3$, $R_2$ is $C_{12}H_{25}$, $R_3$ is selected from the group consisting of $C_4H_9$, $C_8H_7$, $C_2H_{25}$, and $C_{16}H_{33}$, and M is H or Na.

11. The composition according to claim 9, wherein the polymer is represented by the following structure:

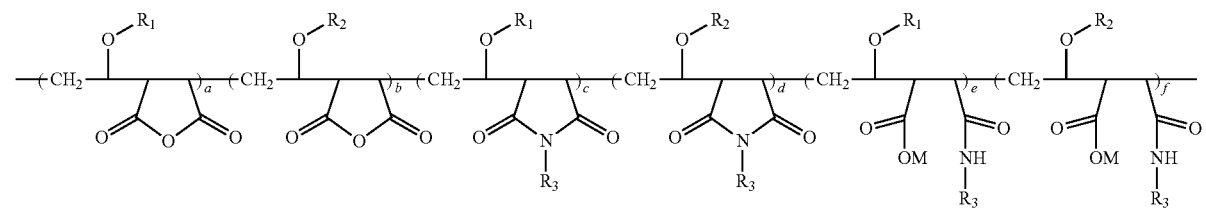

wherein $R_1$ is a $C_1$-$C_7$ alkyl group, $R_2$ is a $C_8$-$C_{30}$ alkyl group, $R_3$ is a $C_1$-$C_{30}$ alkyl group, and M is selected from the group consisting of hydrogen, alkali metals, alkaline earth metals, ammonium salts, and combinations thereof, wherein a, b, c, d, e, and f are molar amounts, the sum of which equals 100%, providing that c and d are not both zero at the same time.

12. The composition according to claim 11, wherein the polymer is represented by the following structure:

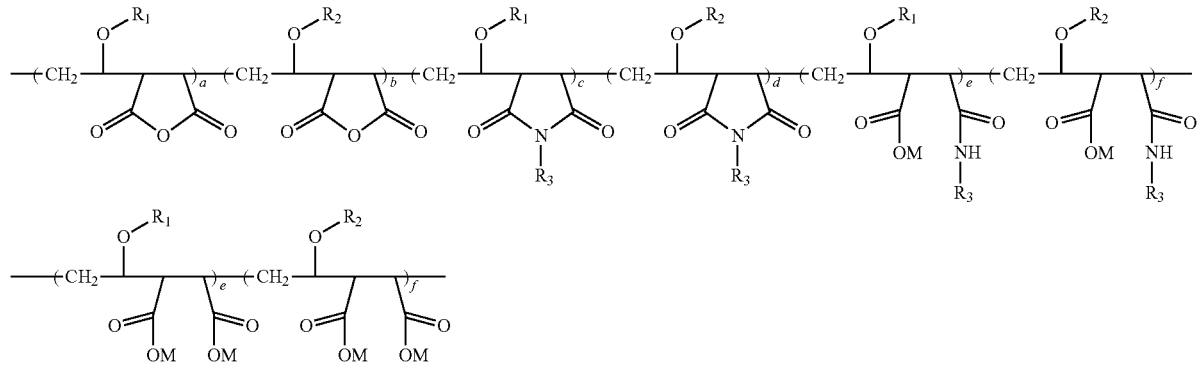

wherein $R_1$ is a $C_1$-$C_7$ alkyl group, $R_2$ is a $C_8$-$C_{30}$ alkyl group, $R_3$ is a $C_1$-$C_{30}$ alkyl group, and M is selected from the group consisting of hydrogen, alkali metals, alkaline earth metals, ammonium salts, and combinations thereof, wherein a, b, c, d, e, and f are molar amounts, the sum of which equals 100%, providing that c and d are not both zero at the same time and e and f are not both zero at the same time.

13. The composition according to claim 11, selected from the group consisting of:

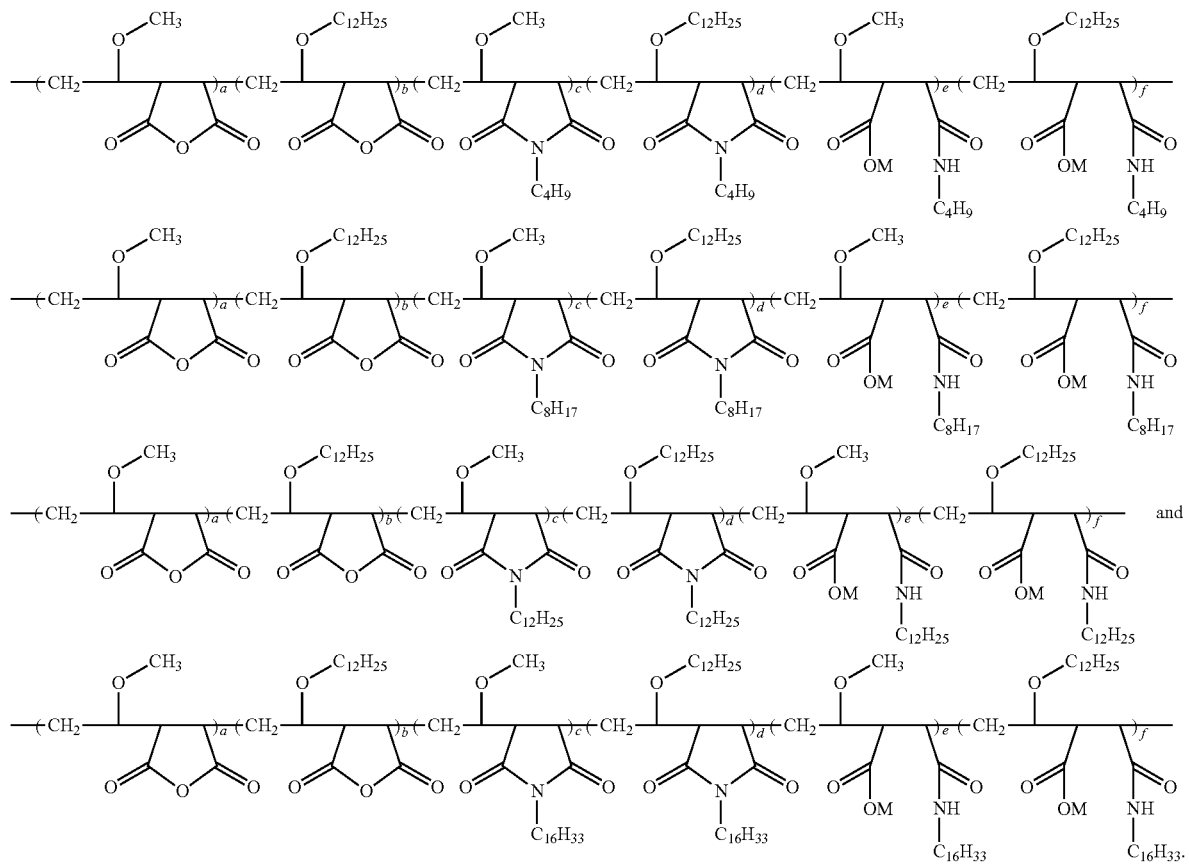

14. The composition according to claim 7, wherein the composition is selected from the group consisting of adhesives, aerosols, agricultural agents, anti-soil redeposition agents, battery agents, beverages, biocides, cementing agents, cleaning agents, coating agents, conductive materials, cosmetic agents, dental agents, detergents, dispersants, drugs, electronics, encapsulations, foods, hair sprays, household-industrial agents, inks and coatings, interlaminate adhesives, lithographic solutions, membrane additive agents, metal working fluids, oilfield agents, paints, paper agents, personal care agents, pharmaceuticals, pigments, plasters, plastics, printing agents, reactive biocides, reactive rheology modifiers, refractive index modifiers, sequestrants, soil release agents, static control agents, and wood-care agents.

15. The composition according to claim 14, wherein the personal care agent composition is selected from the group consisting of adhesives, antiperspirants and deodorants, cosmetics, drug delivery systems, facial compositions, hair compositions, modified natural oils, oil compositions, oral care agents, pharmaceutical compositions, pigments, skin and tissue compositions, sun care products, tablet coatings, thermal protection, toothpaste compositions, transdermal patches, wear resistance, and wrinkle reduction.

* * * * *